(12) United States Patent (10) Patent No.: US 8,841,388 B2
Lin et al. (45) Date of Patent: Sep. 23, 2014

(54) MONOFUNCTIONAL, BIFUNCTIONAL, AND MULTIFUNCTIONAL PHOSPHINATED PHENOLS AND THEIR DERIVATIVES AND PREPARATION METHOD THEREOF

(75) Inventors: Ching-Hsuan Lin, Taichung (TW); Yu-Wei Tian, Taichung (TW)

(73) Assignee: National Chung Hsing University, Taichung (TW)

( * ) Notice: Subject to any disclaimer, the term of this patent is extended or adjusted under 35 U.S.C. 154(b) by 64 days.

(21) Appl. No.: 13/542,556

(22) Filed: Jul. 5, 2012

(65) Prior Publication Data

US 2013/0012668 A1 Jan. 10, 2013

(30) Foreign Application Priority Data

Jul. 6, 2011 (TW) .............................. 100123924 A

(51) Int. Cl.
   *C07F 9/6571* (2006.01)
   *C08L 63/04* (2006.01)
   *C08G 59/06* (2006.01)
   *C08G 59/62* (2006.01)
   *C08G 59/32* (2006.01)

(52) U.S. Cl.
   CPC ........... *C07F 9/657172* (2013.01); *C08L 63/04* (2013.01); *C08G 59/063* (2013.01); *C08G 59/621* (2013.01); *C08G 59/3272* (2013.01)
   USPC ....................................................... 525/481

(58) Field of Classification Search
   USPC ............................................. 558/76; 514/111
   See application file for complete search history.

(56) References Cited

U.S. PATENT DOCUMENTS

2004/0077821 A1  4/2004  Hwang et al.
2010/0016585 A1  1/2010  Lin et al.

FOREIGN PATENT DOCUMENTS

| EP | 1544227 A1 | 6/2005 |
| JP | 2001-294759 A | 10/2001 |
| TW | 575633 B | 2/2004 |
| TW | 2010-02732 A | 1/2010 |

(Continued)

OTHER PUBLICATIONS

C.S. Wang et al., "Synthesis and Properties of Phosphorus-Containing PEN and PPN Copolyesters," Polymer, 40, (1999), pp. 747-757.

(Continued)

*Primary Examiner* — Taofiq A Solola
(74) *Attorney, Agent, or Firm* — Juan Carlos A. Marquez; Bacon & Thomas PLLC

(57) ABSTRACT

The present invention provides novel phosphinated compounds of monofunctional, bifunctional, multifunctional phenols represented by the following formulae and their derivatives, and preparation methods thereof:

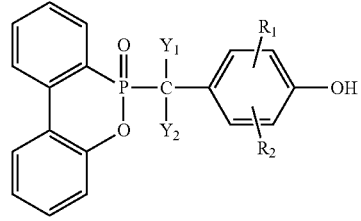

(I)

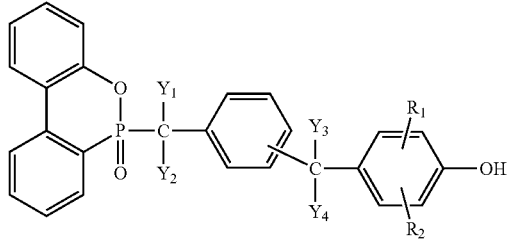

(II)

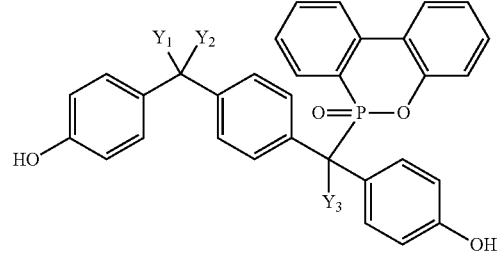

(III)

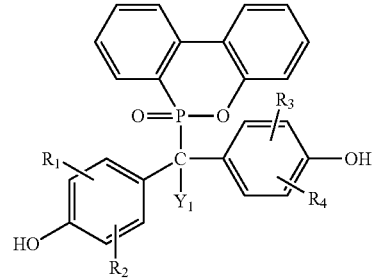

(IV)

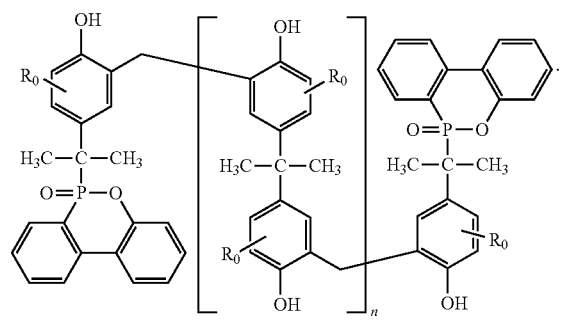

(V)

16 Claims, 3 Drawing Sheets

(56) References Cited

FOREIGN PATENT DOCUMENTS

| TW | 2010-41927 A | 12/2010 |
|---|---|---|
| WO | WO 2010-114302 A2 | 10/2010 |
| WO | WO 2010/135393 A1 | 11/2010 |

OTHER PUBLICATIONS

C.H. Lin et al., "Novel Phosphorus-Containing Epoxy Resins Part I. Synthesis and Properties," Polymer, 42 (2001) pp. 1869-1878.

C.H. Lin et al., "Synthesis and Properties of Phosphorus-Containing Advanced Epoxy Resins, II," Journal of Applied Polymer Science, vol. 78, (2000), pp. 228-235.

C.H. Lin et al., "Synthesis and Property of Phosphorus-Containing Bismaleimide by a Novel Method," Journal of Polymer Science: Part A: Polymer Chemistry, vol. 38, (2000), pp. 2260-2268.

Y.L. Liu et al., "Synthesis and Properties of New Organosoluble Aromatic Polyamides with Cyclic Bulky Groups Containing Phosphorus," Polymer, 43 (2002) pp. 5757-5762.

C.S. Wu et al. "Synthesis and Characterization of New Organosoluble Polyaspartimides Containing Phosphorus," Polymer, 43 (2002) pp. 1773-1779.

Y.L. Liu et al., "Flame Retardant Epoxy Resins From o-Cresol Novolac Epoxy Cured With a Phosphorus-Containing Aralkyl Novolac," Journal of Polymer Science: Part A: Polymer Chemistry, vol. 40, (2002) pp. 2329-2339.

H.L. Ching et al., "Flame-Retardant Epoxy Resins with High Glass-Transition Temperatures. II. Using a Novel Hexafunctional Curing Agent: 9, 10-Dihydro-9-oxa-10-phosphaphenanthrene 10-yl-tris(4-aminophenyl) methane," Journal of Polymer Science: Part A: Polymer Chemistry, vol. 43 (2005) pp. 5971-5986.

S.X. Cai et al., "Flame-Retardant Epoxy Resins With High Glass-Transition Temperatures from a Novel Trifunctional Curing Agent: Dopotriol," Journal of Polymer Science: Part A: Polymer Chemistry, vol. 43, (2005), pp. 2862-2873.

C.H. Lin et al., "Facile Preparation of Novel Epoxy Curing Agents and Their High-Performance Thermosets," Journal of Polymer Science: Part A: Polymer Chemistry, vol. 46, (2008), pp. 7898-7912.

A.J. Caruso et al., "A New Reaction of Bisphenol A and Preparation of Polysubstituted 9, 9-Dimethylxanthenes," J. Org. Chem. vol. 62, (1997), pp. 1058-1063.

Office Action and Search Report issued from Taiwan Intellectual Property Office in corresponding ROC Taiwan Patent Application No. 100123924, dated May 30, 2013, pp. 1-6.

MONOFUNCTIONAL, BIFUNCTIONAL, AND MULTIFUNCTIONAL PHOSPHINATED PHENOLS AND THEIR DERIVATIVES AND PREPARATION METHOD THEREOF

FIELD OF THE INVENTION

The present invention relates to novel phosphinated compounds of monofunctional, bifunctional, and multifunctional phenols (or monofunctional, bifunctional, and multifunctional phosphinated phenols) and their epoxy resin, benzoxazine, and cyanate derivatives, and preparation methods thereof. The phosphinated compounds may be further used to prepare a cured flame-resistant resin.

DESCRIPTION OF THE RELATED ART

Epoxy resin has the advantages of excellent electrical properties, dimensional stability, high-temperature resistance, solvent resistance, low cost, and high adherence, and is useful as a printed circuit board and integrated circuit package material. However, like common plastics materials, epoxy resin formed of bonded carbon, hydrogen, and oxygen atoms is easily flammable, and hazardous. Therefore, strict flame resistance standards are set for use of electronic and information materials in various parts of the world.

The prevailing prior art technique for rendering epoxy resin flame retardant is through introduction of bromine atoms. Due to excellent flame resistant characteristics, bromine-containing epoxy resins are widely used in electronic materials requiring flame resistant characteristics. However, in the combustion process of the bromine-containing epoxy resins, corrosive and toxic substances are released such as hydrogen bromide, tetrabromodibenzo-p-dioxin, and tetrabromodibenzofuran.

Besides halogen-containing compounds, organophosphorus compounds also have high flame retardance. In combustion, a phosphinated flame resistant agent promotes dehydration of polymer materials, through a process in which hydrogen of hydrocarbons reacts with oxygen in the air to form water. As a result, ambient temperature is reduced lower than the combustion temperature, thereby achieving the flame resistant effect. On the other hand, when heated at a high temperature, the phosphinated flame resistant agent decomposes, releasing phosphoric acid, which promotes the carbonation of polymers, thus forming an incombustible layer of coke. Additionally, phosphoric acid is further dehydrated and esterified at high temperature to form polyphosphoric acid, which covers the surface of the comburent, thus exerting a protective effect by preventing oxygen gas from entering the uncombusted inner side of the polymer, and inhibiting the release of volatile cracking products.

Two methods are used to introduce phosphorus: one is directly synthesizing a phosphinated epoxy resin, and the other is mixing uniformly a phosphinated curing agent and an epoxy resin. The present invention provides a phosphinated curing agent for mixing with and curing an epoxy resin so as to achieve the flame resistant effect.

Among phosphinated derivatives, 9,10-dihydro-9-oxa-10-phosphaphenanthrene 10-oxide (DOPO) attracts particular attention because it can undergo a nucleophilic addition with electron-deficient compounds such as benzoquinone[1], oxirane[2], maleic acid[3], bismaleimide[4], diaminobenzophenone[5-6], and terephthaldicarboxaldehyde[7].

In 2001, Wang et. al. proposed that DOPO might directly react with the epoxy group of a bifunctional or multifunctional epoxy resin through addition of the active hydrogen of the DOPO to form a semi-cured flame resistant epoxy resin that has a high glass transition temperature (Tg), a high pyrolysis temperature and a high elasticity and is environmentally friendly[2]. In 2005, Lin et. al. disclosed a synthesis method and application of trifunctional curing agents (dopotriol[8] and dopo-ta[9]), in which a flame resistant epoxy resin having a high glass transition temperature was obtained. However, the raw material for synthesis of dopotriol, namely, rosolic acid, is costly, so the method is uneconomic in industrial applications. Then, in 2008, Lin et. al. used 4,4'-dihydroxy benzophenone (DHBP) and DOPO, which are much cheaper, to react with phenol/aniline, and successfully synthesized phosphinated flame resistant dopotriol and dopodiolamine[10]. The cured epoxy resin has excellent glass transition temperature, thermostability, dimensional stability and flame resistance. However, the solubility of dopotriol and dopodiolamine is poor.

Novolac resin was the first synthetic resin employed in industrial applications. As the raw material is readily available, its water absorption is low, its processability is excellent, and the performance of the cured resin satisfies many practical requirements, novolac resin is widely used in mold plastics, insulation materials, paints, and wood bonding. Increasingly stringent safety standards have generated interest recently in novolac resin with favorable flame retardant, non-toxic, and low smoke generating properties, especially in applications in facilities such as airports, train stations, schools, hospitals, and other public buildings and aircraft interiors.

It is pointed out in literatures that bisphenol A is catalyzed by an acid to degrade into phenol and unstable 4-isopropenylphenolt[11]. In the present invention, DOPO and bisphenol A are reacted in the presence of an acid catalyst, so that DOPO is bonded to the newly formed 4-isopropenylphenol, to synthesize monofunctional phenolic compounds. Next, DOPO and trifunctional phenol 1,1,1-tris(4-hydroxyphenyl)ethane are reacted in the presence of an acid catalyst, to form a bifunctional phenolic compound. Additionally, in the present invention, DOPO and multifunctional bisphenol A novolac resin (BPA novolac) are reacted in the presence of an acid catalyst, to synthesize a phosphinated multifunctional bisphenol A novolac resin. In the present invention, phosphinated phenols further undergo reactions to form epoxy resin, benzoxazine and cyanate derivatives.

REFERENCES

[1] Wang, C. S. and Lin, C. H. Polymer 1999; 40; 747.
[2] Lin, C. H. and Wang, C. S. Polymer., 2001, 42, 1869.
[3] Wang, C. S.; Lin, C. H. and Wu, C. Y. J. Appl. Polym. Sci. 2000, 78, 228.
[4] Lin, C. H. and Wang, C. S. J. Polym. Sci. Part A: Polym. Chem. 2000, 38, 2260.
[5] Liu, Y. L. and Tsai, S. H. Polymer 2002; 43; 5757.
[6] Wu, C. S.; Liu, Y. L. and Chiu, Y. S. Polymer 2002; 43; 1773.
[7] Liu, Y. L.; Wang, C. S.; Hsu, K. Y. and Chang, T. C. J. Polym. Sci. Part A: Polym. Chem. 2002, 40, 2329.
[8] Lin, C. H.; Cai, S. X. and Lin, C. H. J. Polym. Sci. Polym. Chem. 2005, 43, 5971.
[9] Cai, S. X. and Lin, C. H. J. Polym. Sci. Polym. Chem. 2005, 43, 2862.
[10] Lin, C. H.; Lin, T. L.; Chang S. L.; Dai, S. H. A.; Cheng, R. J.; Hwang, K. U.; Tu, A. P.; Su, W. C. J. Polym. Sci. Part A: Polym. Chem. 2008, 46, 7898.

[11] Andrew J. C. and Julia L. L. J. Org. Chem. 1997, 62, 1058.

BRIEF SUMMARY OF THE INVENTION

The present invention is directed to a preparation method of novel phosphinated compounds of monofunctional, bifunctional, and multifunctional phenols and their epoxy resin, benzoxazine and cyanate derivatives. The phosphinated compounds may be further used to prepare a cured flame-resistant resin.

DETAILED DESCRIPTION OF THE INVENTION

Figure 1:
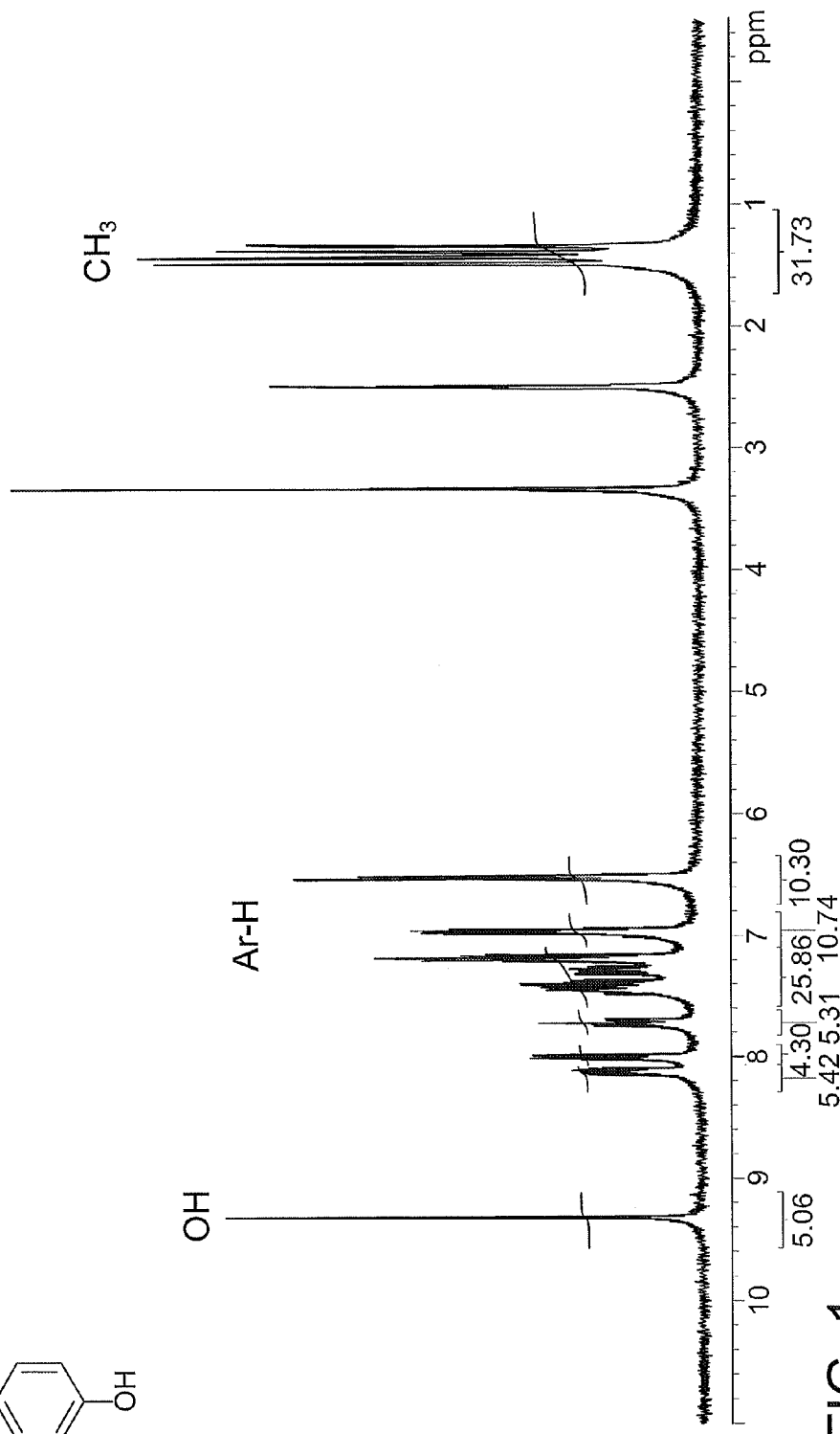
FIG. 1 is a $^1$H NMR spectrum of compound A.
Figure 1:
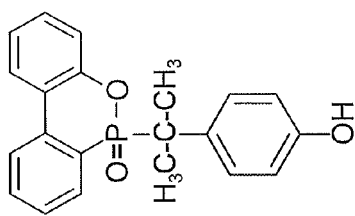

In the specification and claims, the singular forms "a," "an," and "the" include the plural unless the context clearly dictates otherwise. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Novel Phosphinated Compounds of Monofunctional and Bifunctional Phenols and Novolac Resin The present invention discloses phosphinated phenolic compounds having a structure represented by the following chemical formulae:

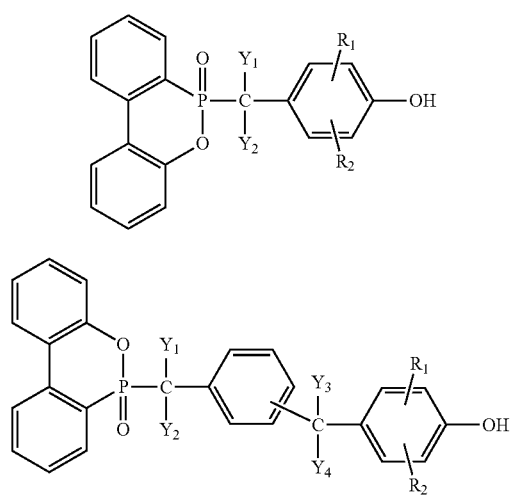

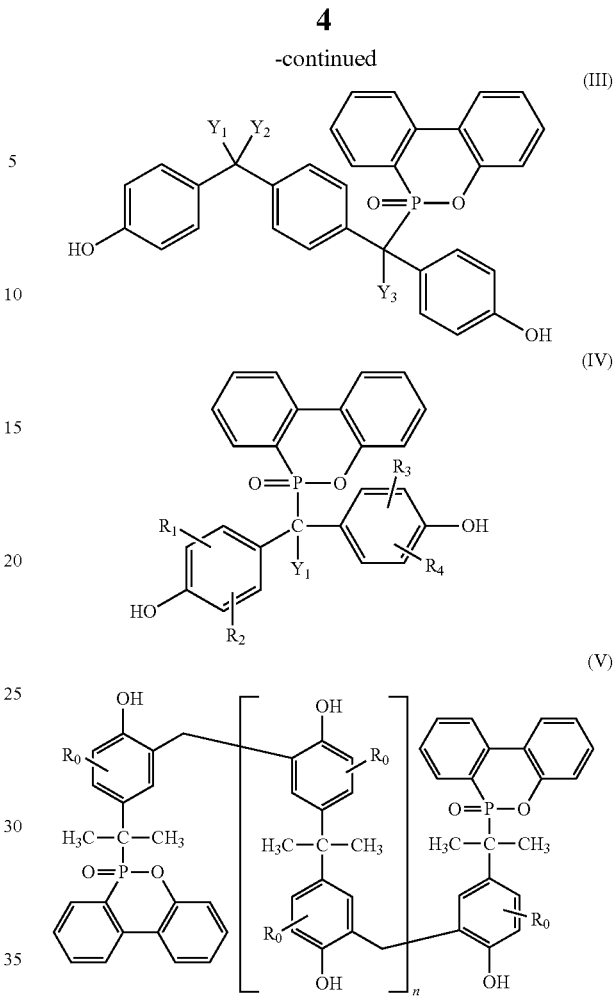

where
$Y_1$ to $Y_4$ are each independently H, a $C_1$-$C_6$ alkyl or phenyl, and preferably methyl;
$R_0$ and $R_4$ are each independently H, a $C_1$-$C_6$ alkyl, a $C_3$-$C_6$ cycloalkyl, F, Cl, Br or I; and
n is an integer of 1 to 10.

When $Y_1$ and $Y_2$ of the compound of formula (I) are $CH_3$, and $R_1$ and $R_2$ are H, the structural formula of the compound of formula (I) may be Compound A of monofunctional phosphinated phenol.

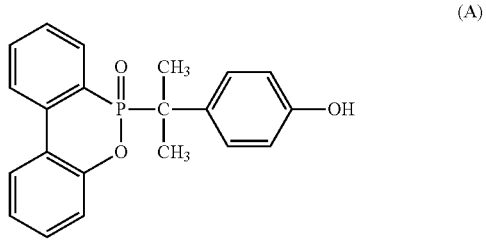 [SMILES: CC(C)(c1ccc(O)cc1)P1(=O)Oc2ccccc2-c2ccccc21]

When $Y_1$ to $Y_4$ of the compound of formula (II) are $CH_3$, $R_1$ and $R_2$ are H, and substituents on the middle benzene ring are in a meta-position relationship, the structural formula of the compound of formula (II) may be Compound B of monofunctional phosphinated phenol.

(B)

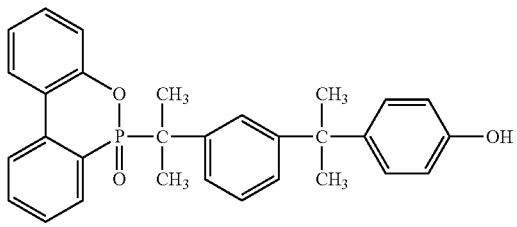

When $Y_1$ to $Y_4$ of the compound of formula (II) are $CH_3$, $R_1$ and $R_2$ are $CH_3$, and substituents on the middle benzene ring are in a para-position relationship, the structural formula of the compound of formula (II) may be Compound C of monofunctional phosphinated phenol.

(C)

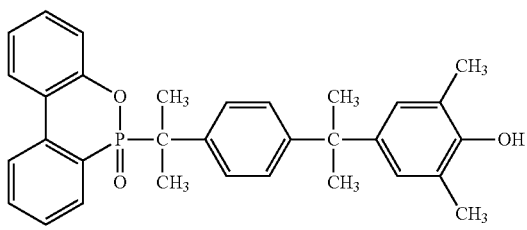

When $Y_1$ to $Y_3$ of the compound of formula (III) are $CH_3$, the structural formula of the compound of formula (III) may be Compound D of bifunctional phosphinated phenol.

(D)

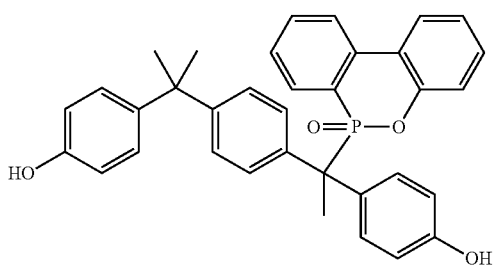

When $Y_1$ of the compound of formula (IV) is $CH_3$, $R_1$ to $R_4$ are H, the structural formula of the compound of formula (IV) may be Compound E of bifunctional phosphinated phenol (being a known compound).

(E)

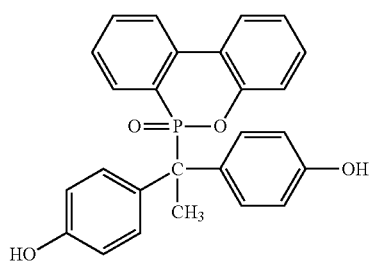

When $R_0$ of the compound of formula (V) is H, the structural formula of the compound of formula (V) may be a phosphinated novolac resin of formula P-BPN.

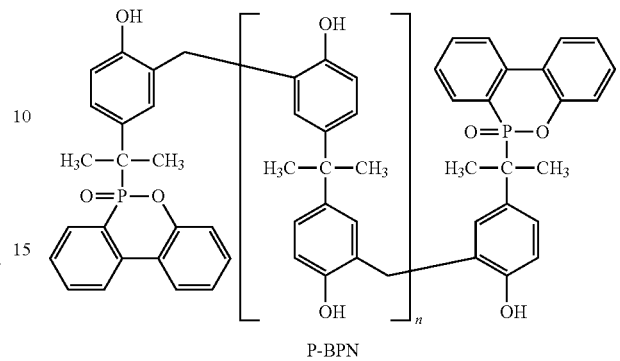

P-BPN

It can be known from the embodiments of the present invention that, when the molecular weight of P-BPN is higher, the glass transition temperature of the corresponding cured product is higher.

Preparation Method of Novel Phosphinated Compounds of Monofunctional and Bifunctional Phenols and Novolac Resin The present invention provides a method for preparing monofunctional, bifunctional, or multifunctional phosphinated phenols, including: in the presence of an acid catalyst, reacting a DOPO compound of the formula below:

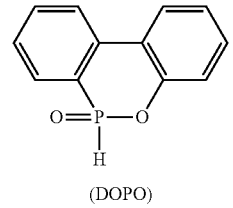 [SMILES: O=[PH]1Oc2ccccc2-c2ccccc21 ; "(DOPO)"]

(DOPO)

with a compound selected from the group consisting of phenolic compounds of the formulae below:

(I)-a

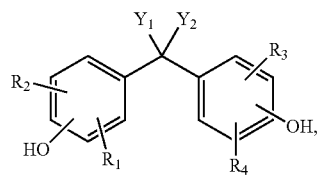

(II)-a

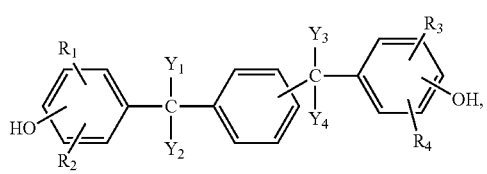

-continued

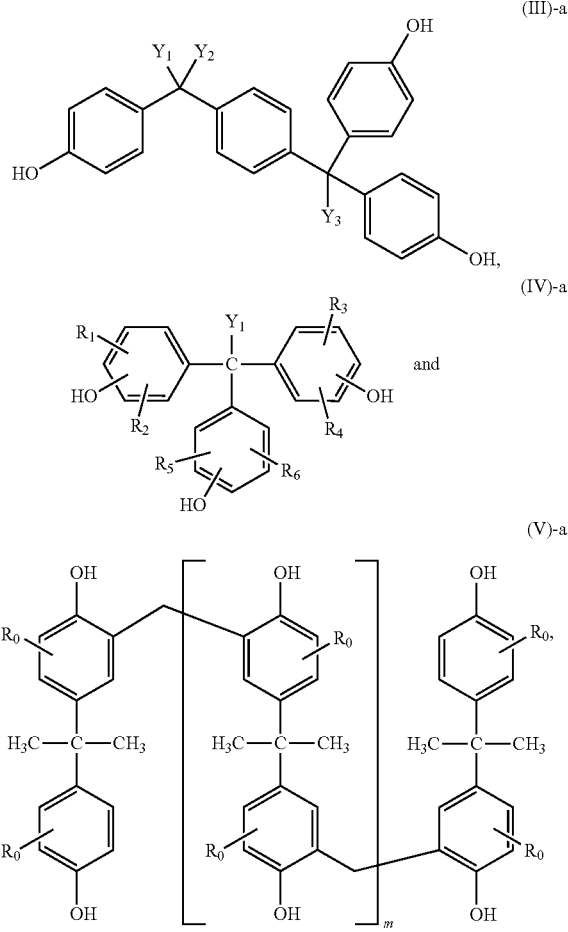

where $Y_1$ to $Y_4$ are each independently H, a $C_1$-$C_6$ alkyl or phenyl, and preferably methyl; $R_0$ to $R_6$ are each independently H, a $C_1$-$C_6$ alkyl, a $C_3$-$C_6$ cycloalkyl, F, Cl, Br or I, and m is an integer of 1 to 10.

In the method according to the present invention, the acid catalyst may be selected from the group consisting of acetic acid, p-toluenesulfonic acid (PTSA), methanesulfonic acid, fluorosulfonic acid, trifluoromethanesulfonic acid, sulfuric acid, orthanilic acid, 3-pyridinesulfonic acid, sulfanilic acid, hydrogen chloride (HCl), hydrogen bromide (HBr), hydrogen iodide (HI), hydrogen fluoride (HF), trifluoroacetic acid ($CF_3COOH$), nitric acid ($HNO_3$), and phosphoric acid ($H_3PO_4$).

In the method according to the present invention, the amount of the acid catalyst is in the range of 0.1 wt % to 10 wt % of the amount of the phenolic compounds, and preferably 1 wt % to 5 wt %.

In the method according to the present invention, the reaction time is 6 to 24 hours, and preferably 12 to 20 hours.

In the method according to the present invention, the reaction temperature is in the range of 60° C. to 150° C.

In the method according to the present invention, the reaction may be conducted in the presence or absence of a solvent. If the reaction is conducted in the presence of a solvent, the solvent may be selected from ethoxyethanol, methoxyethanol, 1-methoxy-2-propanol, propylene glycol monomethyl ether (DOW PM), dioxane, or a combination thereof.

In the method according to the present invention, when the phenolic compound is the compound of formula (I)-a, where $Y_1$ and $Y_2$ are $CH_3$, and $R_1$ to $R_4$ are H, the chemical reaction formula may be as follows, and the resulting product is Compound A of monofunctional phosphinated phenol.

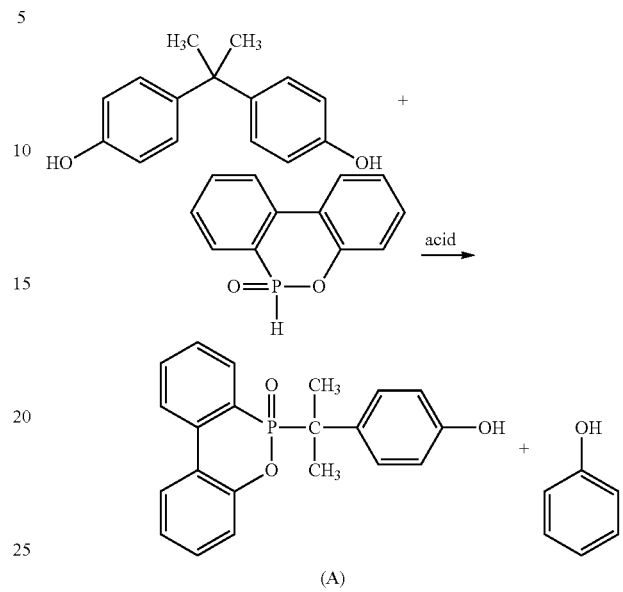

In the method according to the present invention, when the phenolic compound is the compound of formula (II)-a, where $Y_1$ to $Y_4$ are $CH_3$, $R_1$ to $R_4$ are H, and the substituents on the middle benzene ring are in a meta-position relationship, the chemical reaction formula may be as follows, and the resulting product is Compound B of monofunctional phosphinated phenol.

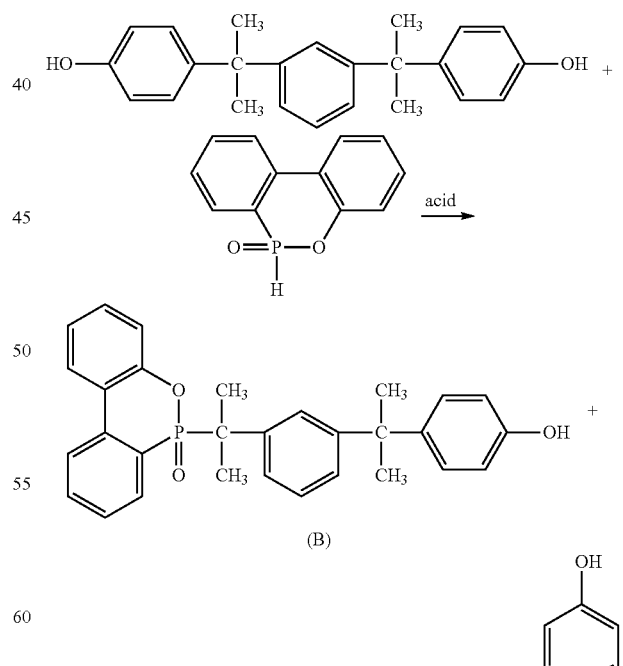

In the method according to the present invention, when the phenolic compound is the compound of formula (II)-a, where $Y_1$ to $Y_4$ are $CH_3$, and $R_1$ to $R_4$ are $CH_3$, and the substituents on the middle benzene ring are in a para-position relationship, the chemical reaction formula may be as follows, and the resulting product is Compound C of monofunctional phosphinated phenol C.

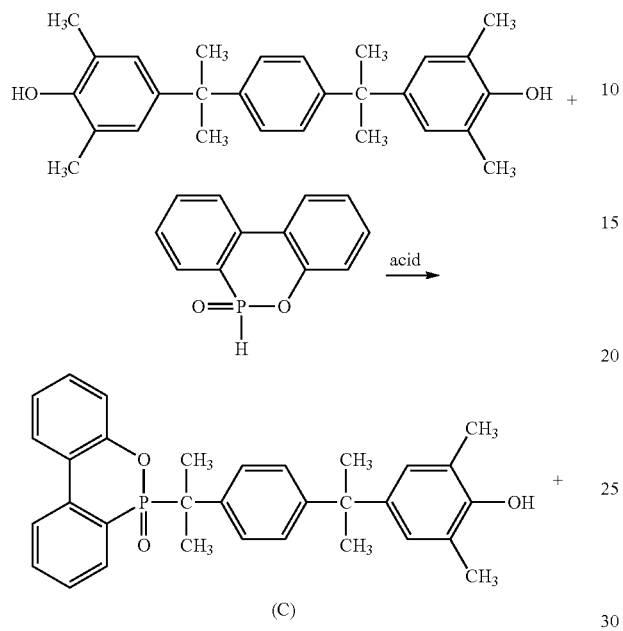

(C)

In the method according to the present invention, when the phenolic compound is the compound of formula (I11)-a, where $Y_1$ to $Y_3$ are $CH_3$, the chemical reaction formula may be as follows, and the resulting product is Compound D of bifunctional phosphinated phenol.

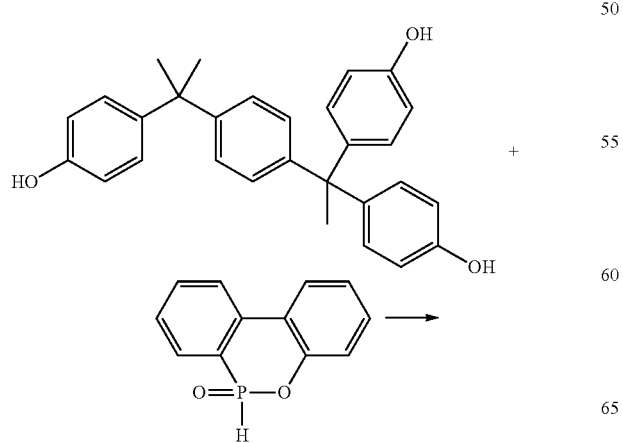

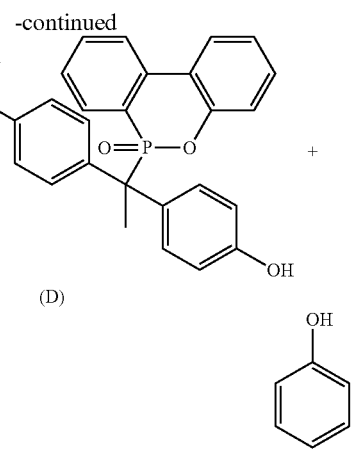

(D)

In the method according to the present invention, when the phenolic compound is the compound of formula (IV)-a, where $Y_1$ is $CH_3$, $R_1$ to $R_6$ are H, the chemical reaction formula may be as follows, and the resulting product is Compound E of bifunctional phosphinated phenol.

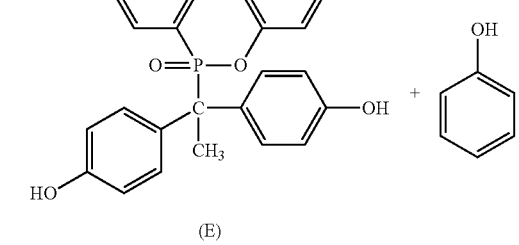

(E)

In the method according to the present invention, when the phenolic compound is the compound of formula (V)-a, where $R_0$ is H, the resulting product is the phosphinated novolac resin of formula P-BPN.

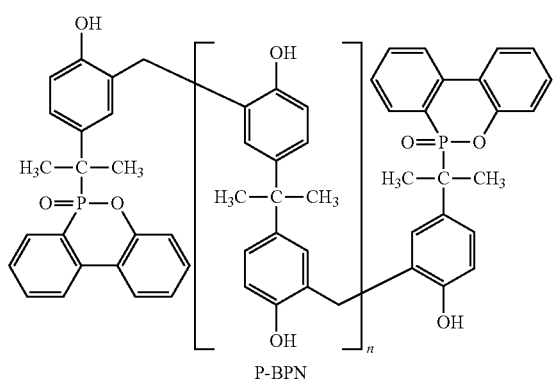
P-BPN

It can be known from the embodiments of the present invention that, in reaction environments of different catalysts, catalyst amounts and reaction temperatures, compounds of formula P-BPN may be generated with different molecular weights. When the amount of the catalyst is reduced from 4% to 2%, a compound of formula P-BPN with a high molecular weight is obtained; and when DOW PM is used as a solvent, a compound P-BPN with a higher molecular weight is obtained.

In application examples of the present invention, the phosphinated compounds of formula P-BPN with different molecular weights may be used as a curing agent of epoxy resin, where the cured products satisfy the flame resistance level V-0 in the UL-94 flammability test. When merely a phosphorus-free compound of formula BPN is used as the curing agent, the cured product is fully combusted in the UL-94 flammability test. Additionally, when the molecular weight of the compound of formula P-BPN is higher, the glass transition temperature of the corresponding cured product is higher.

Novel P-BPN Derivative

The present invention further discloses a P-BPN derivative having a structure of the formulae below:

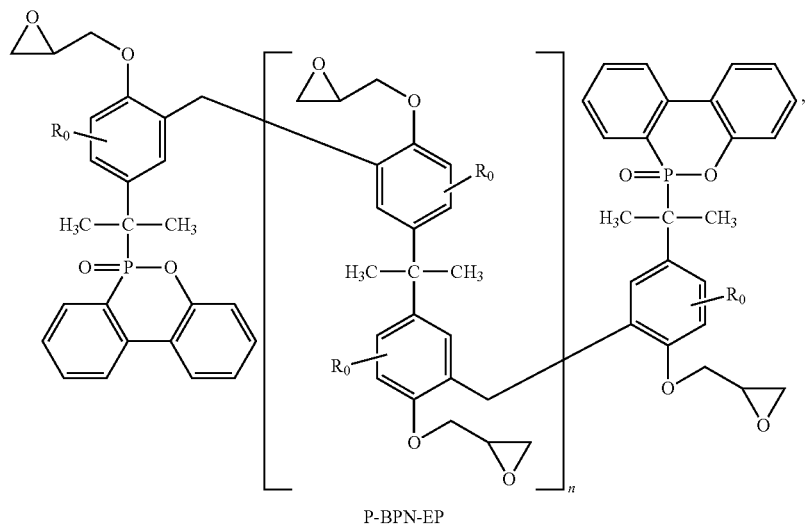
P-BPN-EP

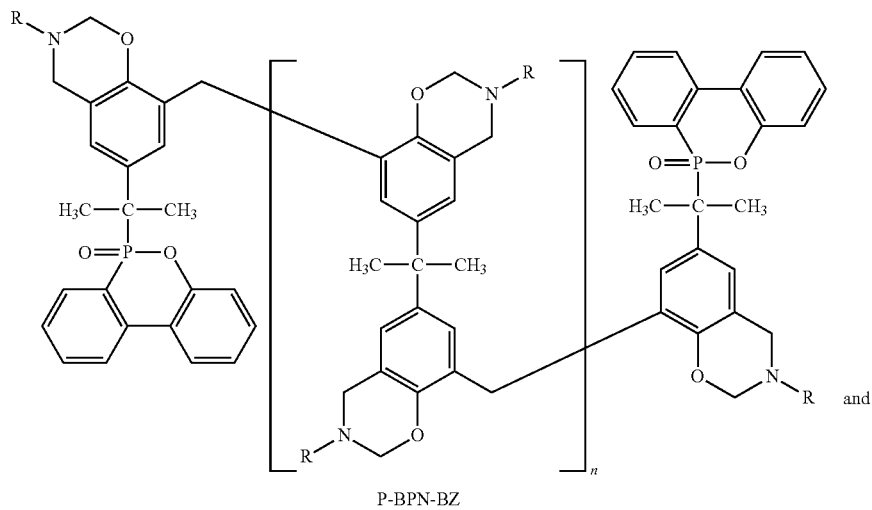
P-BPN-BZ and

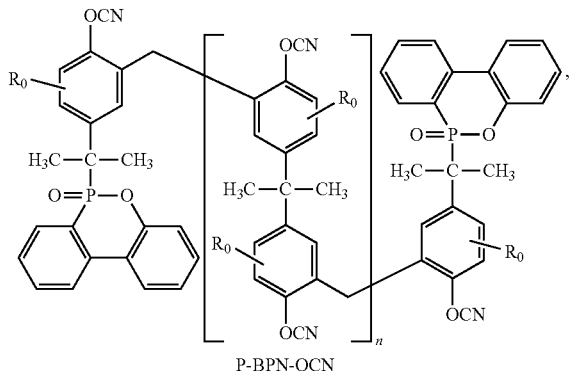
P-BPN-OCN where $R_0$ is H, a $C_1$-$C_6$ alkyl, a $C_3$-$C_5$ cycloalkyl, F, Cl, Br or I, R is selected from the group consisting of a $C_1$-$C_{12}$ alkyl, phenyl, propenyl, N≡C—$C_6H_4$— and HC≡C—O—$C_6H_4$—, and n is an integer of 1 to 10.

When $R_0$ of the compound of formula P-BPN-EP is H, the structural formula of the compound of formula P-BPN-EP may be a compound of formula P-BPN-EP-1.

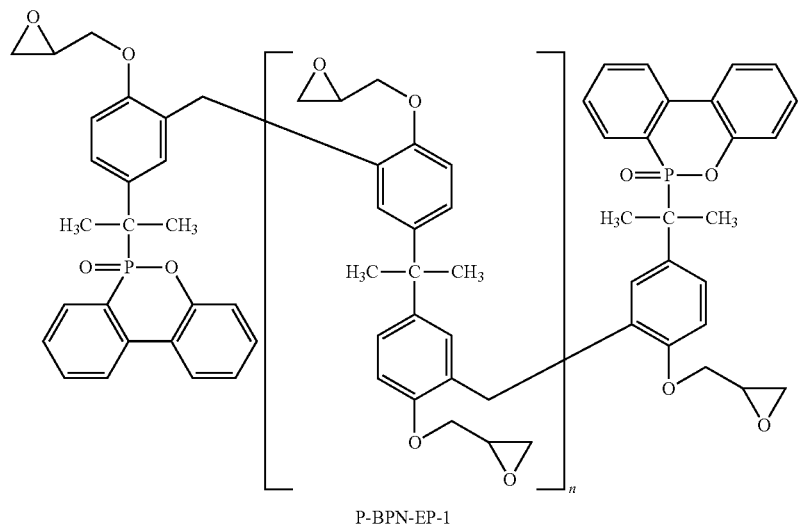
P-BPN-EP-1

When R of the compound of formula P-BPN-BZ is $CH_3$, the structural formula of the compound of formula P-BPN-BZ may be a compound of formula P-BPN-BZ-1.

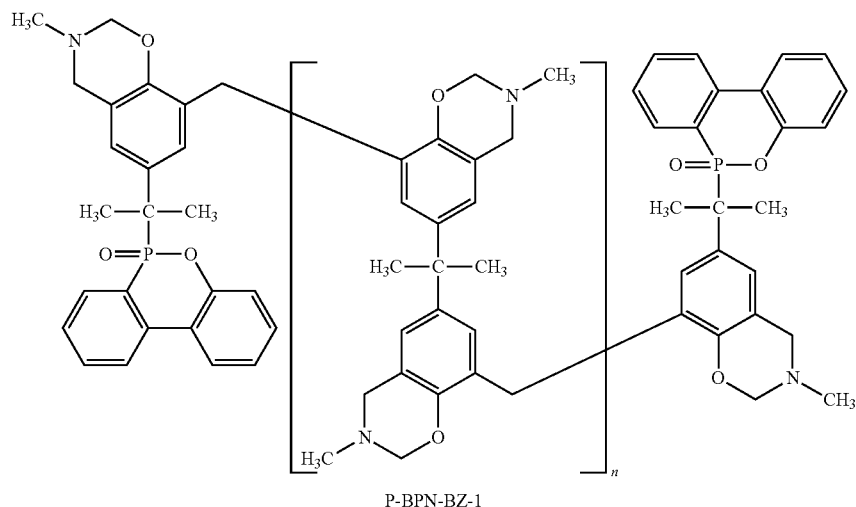

P-BPN-BZ-1

When $R_0$ of the compound of formula P-BPN-OCN is H, the structural formula of the compound of formula P-BPN-OCN may be a compound of formula P-BPN-OCN-1.

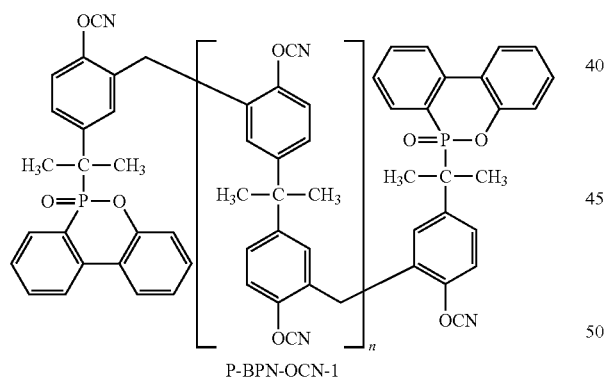

P-BPN-OCN-1

Preparation Method of Novel P-BPN Derivatives

The present invention provides a preparation method for a novel P-BPN derivative, where the derivative may be an epoxy resin derivative (P-BPN-EP), a benzoxazine derivative (P-BPN-BZ), or a cyanate derivative (P-BPN-OCN), and the chemical reactions are as shown below:

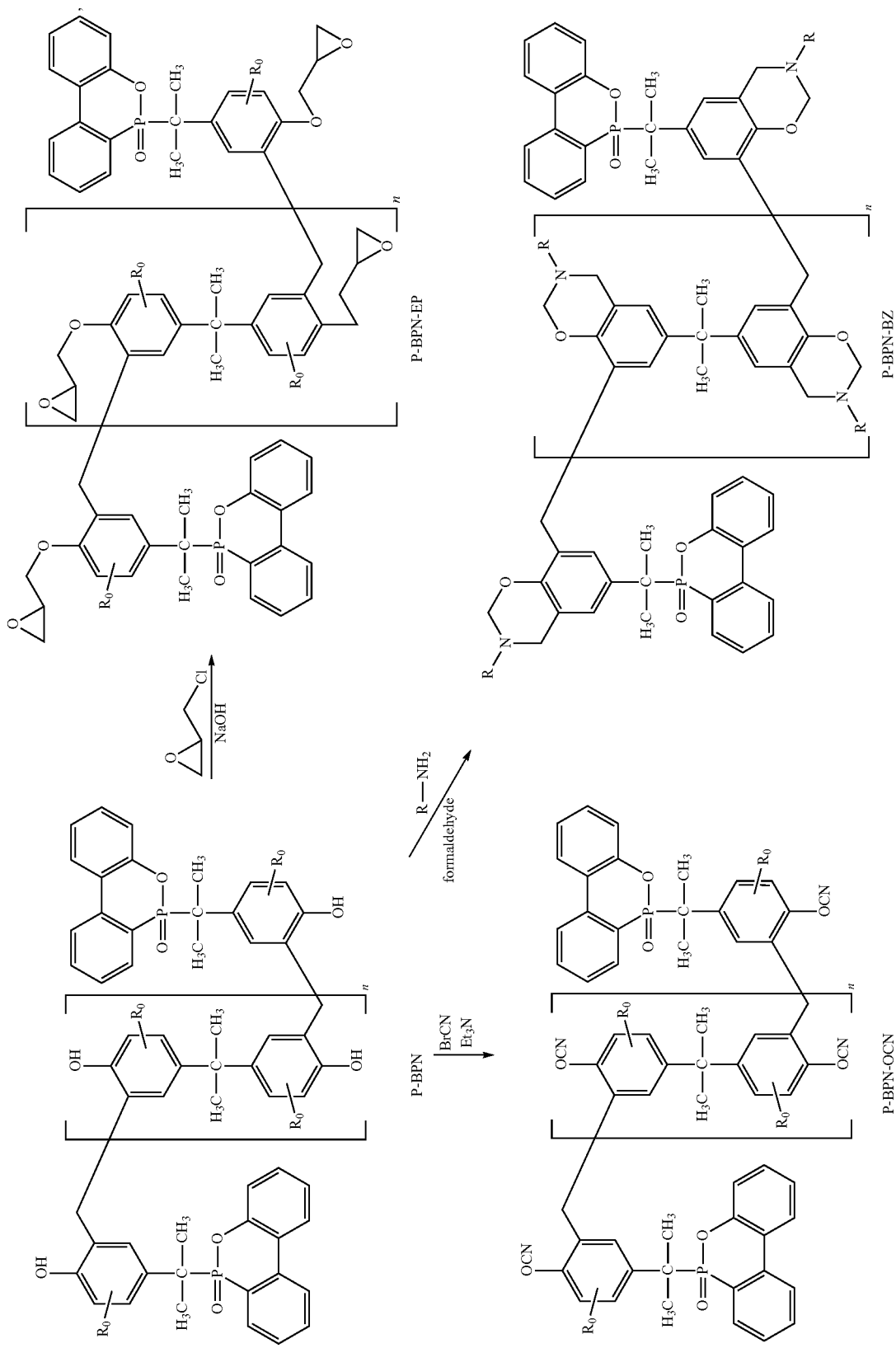

where $R_0$ is H, $C_1$-$C_6$ alkyl, $C_3$-$C_5$ cycloalkyl, F, Cl, Br or I, R is selected from the group consisting of $C_1$-$C_{12}$ alkyl, phenyl, propenyl, N≡C—$C_6H_4$— and HC≡C—O—$C_6H_4$—, and n is an integer of 1 to 10.

In the method according to the present invention, when $R_0$ of the compound of formula P-BPN is H, the resulting products may respectively be an epoxy resin derivative of formula P-BPN-EP-1, a benzoxazine derivative of formula P-BPN-BZ-1, or a cyanate derivative of formula P-BPN-OCN-1.

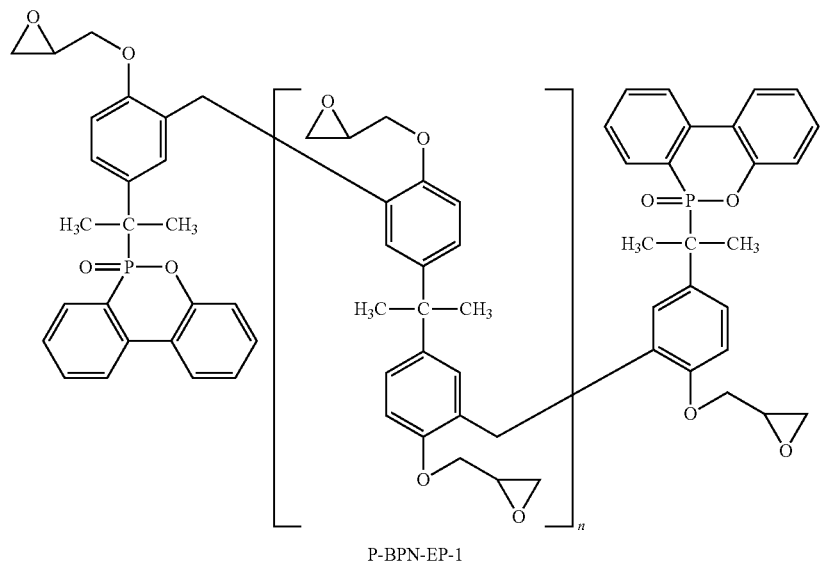

P-BPN-EP-1

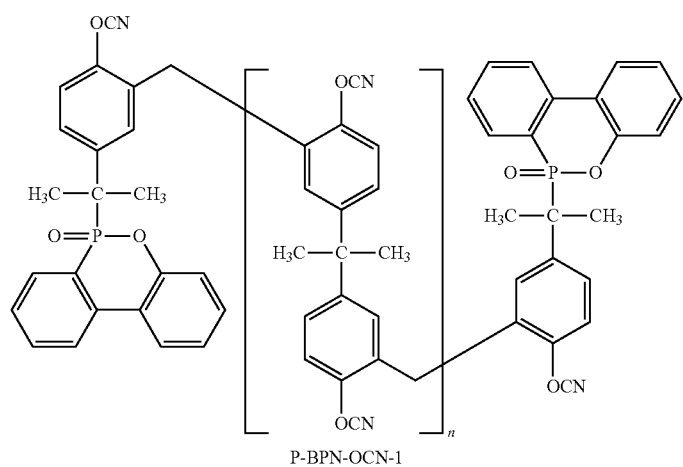

P-BPN-OCN-1

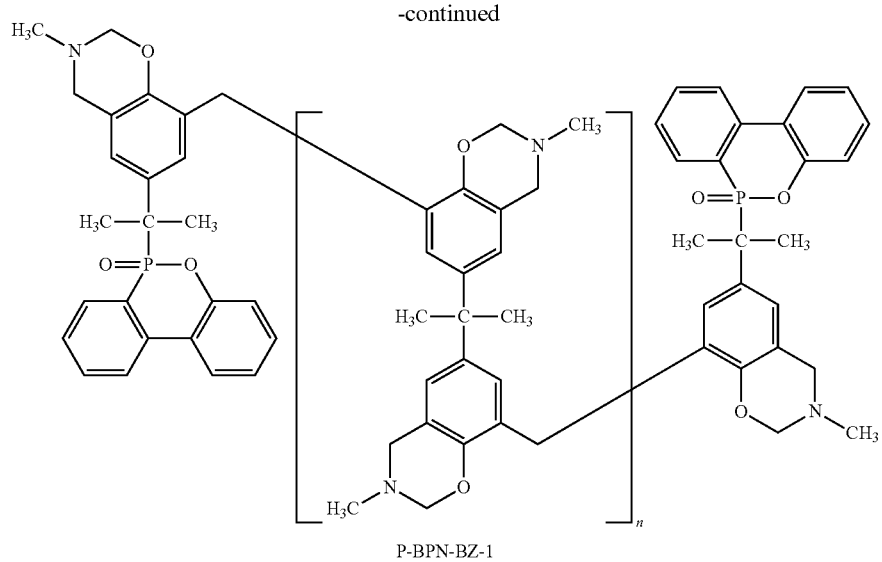

P-BPN-BZ-1

Epoxy Resin Containing Novel Curing Agent

The present invention further provides an epoxy resin containing a curing agent, where the curing agent is one compound selected from the phosphinated compounds of monofunctional, bifunctional, multifunctional phenols, novolac resin, and the derivatives of formula P-BPN.

EXAMPLES

The following embodiments are used to further illustrate the present invention, but not intended to limit the scope of the present invention, and any modifications and variations achieved by those skilled in the art without departing from the spirit of the present invention will fall into the scope of the present invention.

Example 1

Synthesis of Compound A

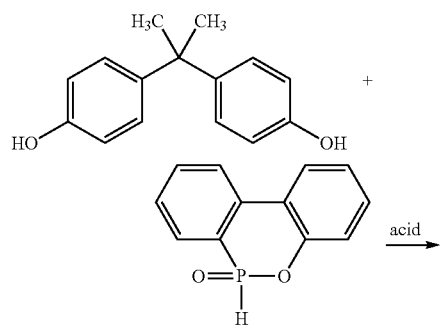

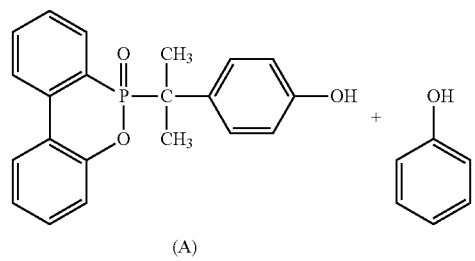

(A)

Monofunctional phosphinated phenol (Compound A) was obtained through reaction of bisphenol A (BPA) and excessive DOPO (9,10-dihydro-9-oxa-10-phosphaphenanthrene 10-oxide) in the presence of an acid catalyst, and the synthesis steps were as follows. To a 0.5 L three-neck reactor equipped with a temperature indicating device, 22.83 g (0.1 mole) of BPA, and 63.85 g (0.3 mole) of DOPO, 0.92 g (BPA of 4 wt %) of toluenesulfonic acid were added, and the reaction temperature was raised to 140° C. The temperature of the reaction system was maintained at 140° C. After 12 hours of reaction, ethanol was added in drops with stirring until precipitation was completed. The mixture was suction-filtered, the precipitate was filtered and separated, and the filter cake was dried in a vacuum oven at 110° C. to give Compound A. The yield was 75%. The molecular formula of Compound A was $C_{21}H_{19}O_3P$, the molecular weight was characterized to be 350.3522 by a high-resolution mass spectrometer. The elemental analysis results were: C: 71.65%, and H: 5.65%. The $^1$H NMR spectrum of Compound A is shown in FIG. 1.

Example 2

Synthesis of Compound B

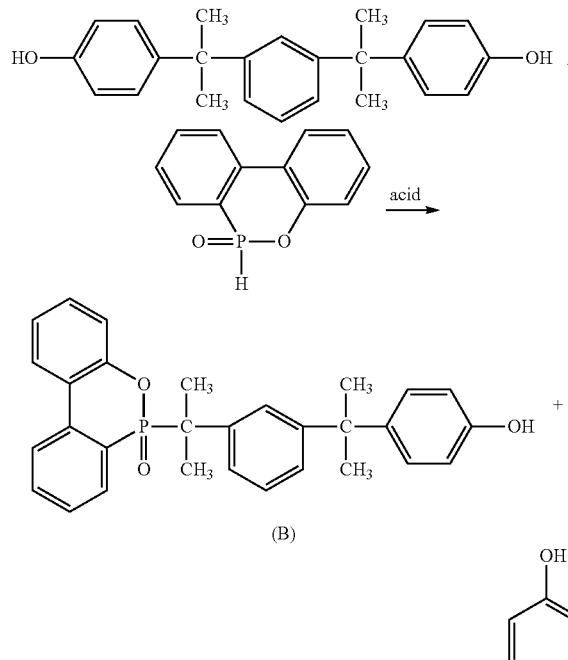

(B)

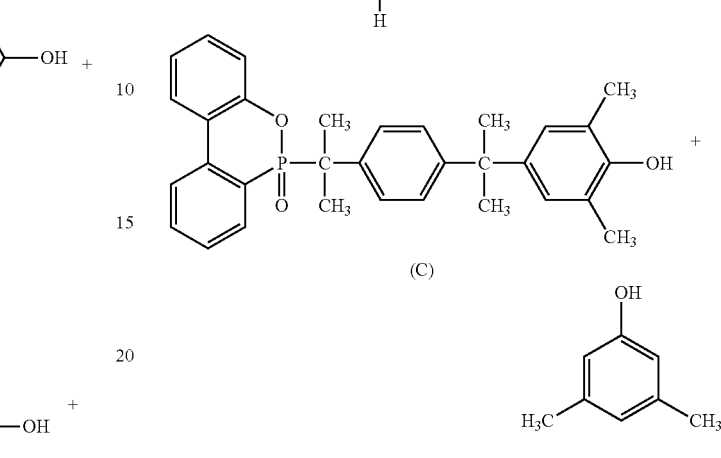

(C)

Monofunctional phosphinated phenol (Compound B) was obtained through reaction of BHPB (1,3-bis[2-(4-hydroxyphenyl)-2-propyl]benzene) and excessive DOPO in the presence of an acid catalyst, and the synthesis steps were as follows. To a 0.5 L three-neck reactor equipped with a temperature indicating device, 34.65 g (0.1 mole) of BHPB, 64.85 g (0.3 mole) of DOPO, and 1.39 g (BHPB of 4 wt %) of sulfuric acid were added, and the reaction temperature was raised to 150° C. The temperature of the reaction system was maintained at 150° C. After 18 hours, ethanol was added in drops with stirring until precipitation was completed. The mixture was suction-filtered, the precipitate was filtered and separated, and the filter cake was dried in a vacuum oven at 110° C. to give Compound B. The yield was 53%. The molecular formula of Compound B was $C_{30}H_{29}O_3P$, and the molecular weight was characterized to be 468.5211 by a high-resolution mass spectrometer. The elemental analysis results were: C: 76.61%, and H: 6.45%.

Example 3

Synthesis of Compound C

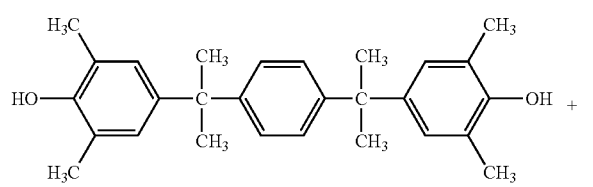

Monofunctional phosphinated phenol (Compound C) was obtained through reaction of BHDMP (alpha,alpha'-bis(4-hydroxy-3,5-dimethylphenyl)-1,4-diisopropylbenzene) and excessive DOPO in the presence of an acid catalyst, and the synthesis steps were as follows. To a 0.5 L three-neck reactor equipped with a temperature indicating device, 40.26 g (0.1 mole) of BHDMP, 64.85 g (0.3 mole) of DOPO, and 3.22 g (BHDMP of 8 wt %) of methanesulfonic acid were added, and the reaction temperature was raised to 180° C. The temperature of the reaction system was maintained at 180° C. After 20 hours, ethanol was added in drops with stirring until precipitation was completed. The mixture was suction-filtered, the precipitate was filtered and separated, and the filter cake was dried in a vacuum oven at 110° C. to give Compound C. The yield was 65%. The molecular formula of Compound C was $C_{32}H_{33}O_3P$, and the molecular weight was characterized to be 496.5823 by a high-resolution mass spectrometer. The elemental analysis results were: C: 77.21%, and H: 6.87%.

Example 4

Synthesis of Compound D

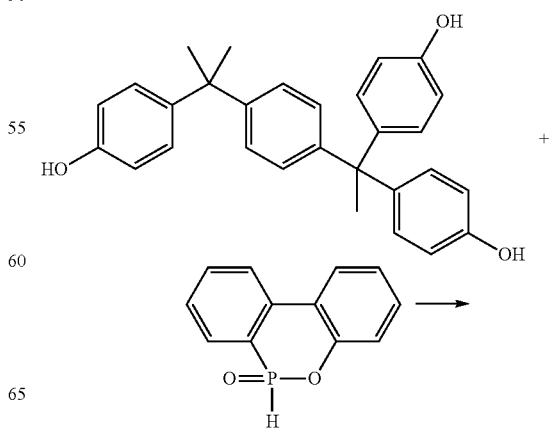

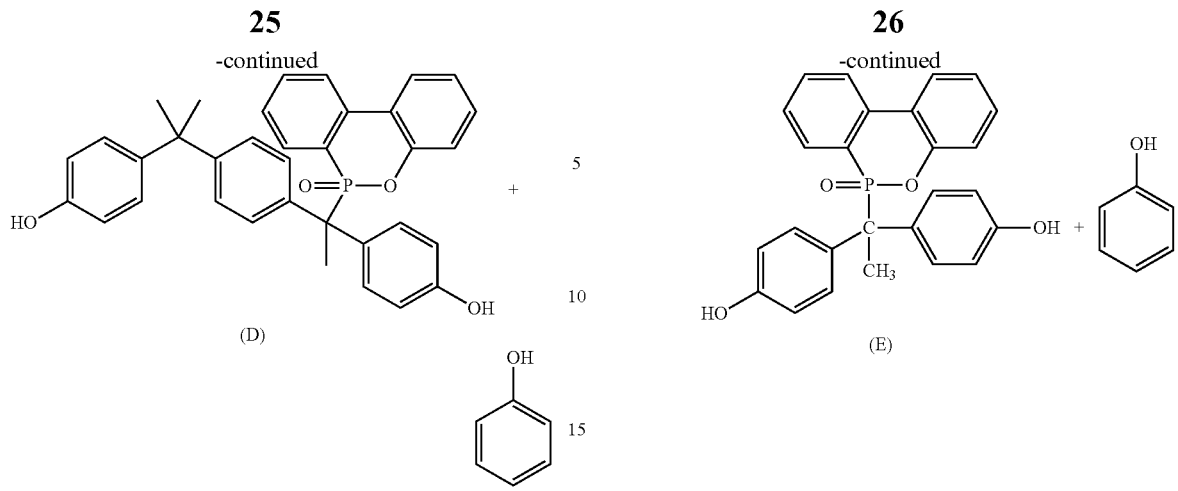

(D)

(E)

Bifunctional phosphinated phenol (Compound D) was obtained through reaction of (trisphenol, PA) monomer and excessive DOPO in the presence of an acid catalyst, and the synthesis steps were as follows. To a 0.5 L three-neck reactor equipped with a temperature indicating device, 42.45 g (0.1 mole) of PA, 63.85 g (0.3 mole) of DOPO, and 1.82 g (PA of 4 wt %) of toluenesulfonic acid were added, and the reaction temperature was raised to 140° C. The temperature of the reaction system was maintained at 140° C. After 16 hours, ethanol was added in drops with stirring until precipitation was completed. The mixture was suction-filtered, the precipitate was filtered and separated, and the filter cake was dried in a vacuum oven at 110° C. to give Compound D. The yield was 78%. The molecular formula of Compound D was $C_{35}H_{31}O_4P$, and the molecular weight was characterized to be 546.5928 by a high-resolution mass spectrometer. The elemental analysis results were: C: 76.77%, and H: 5.88%.

Figure 2:
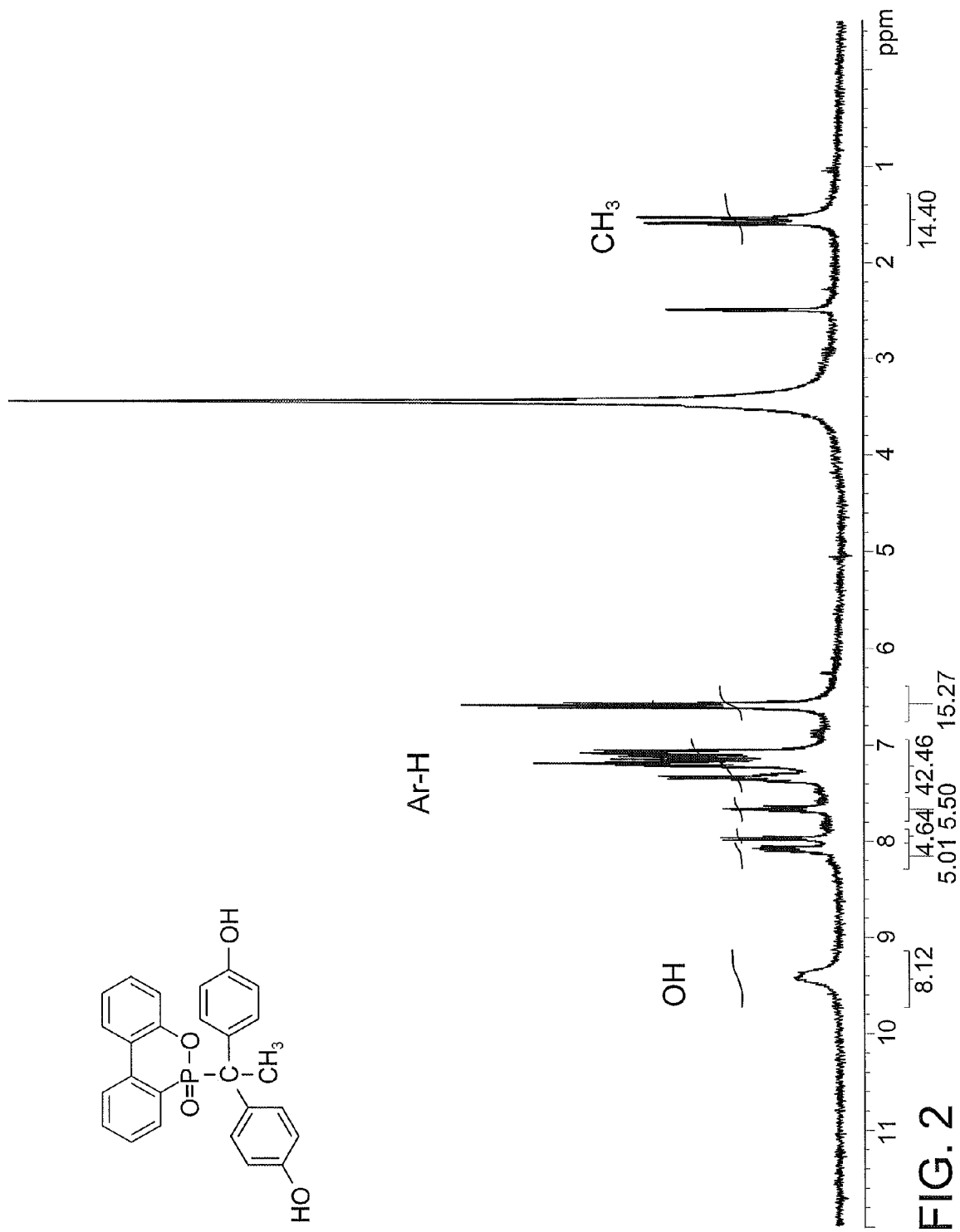
FIG. 2 is a $^1$H NMR spectrum of compound E.

Bifunctional phosphinated phenol (Compound E) was obtained through reaction of a trifunctional phenol monomer THPE (1,1,1-Tris(4-hydroxyphenyl)ethane) and excessively DOPO in the presence of an acid catalyst, and the synthesis steps were as follows. To a 0.5 L three-neck reactor equipped with a temperature indicating device, 30.64 g (0.1 mole) of THPE, 63.85 g (0.3 mole) of DOPO, and 1.23 g (THPE of 4 wt %) of toluenesulfonic acid were added, and the reaction temperature was raised to 130° C. The temperature of the reaction system was maintained at 130° C. After 12 hours, ethanol was added in drops with stirring until precipitation was completed. The mixture was suction-filtered, the precipitate was filtered and separated, and the filter cake was dried in a vacuum oven at 110° C. to give Compound E. The yield was 58%. The molecular formula of Compound E was $C_{26}H_{21}O_4P$, and the molecular weight was characterized to be 428.4213 by a high-resolution mass spectrometer. The elemental analysis results were: C: 72.98%, and H: 5.01%. The $^1$H NMR spectrum of the compound E is shown in FIG. 2.

Example 5

Synthesis of Compound E

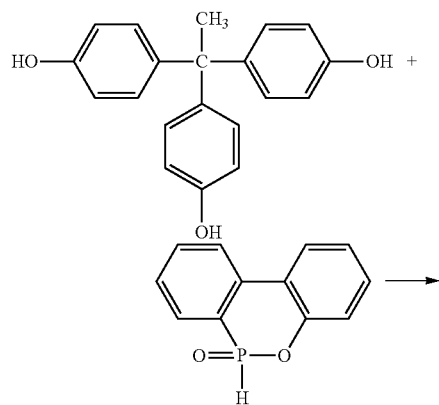

Example 6

Synthesis of Compound P-BPN-2a

A phosphinated novolac resin (P-BPN-2a) having a phosphorus content of 2% was obtained through reaction of bisphenol A novolac (BPN) and DOPO in the presence of an acid catalyst, and the synthesis steps were as follows. To a 0.5 L three-neck reactor equipped with a temperature indicating device, 50 g of BPN, 8.102 g of DOPO and 2 g (BPN of 4 wt %) of toluenesulfonic acid were added. The temperature of the reaction system was maintained at 140° C. After 12 hours, the sticky reaction mixture was washed with aqueous methanol solution to remove residual toluenesulfonic acid, suction-filtered, filtered and separated, and dried in a vacuum oven at 100° C.

Figure 3:
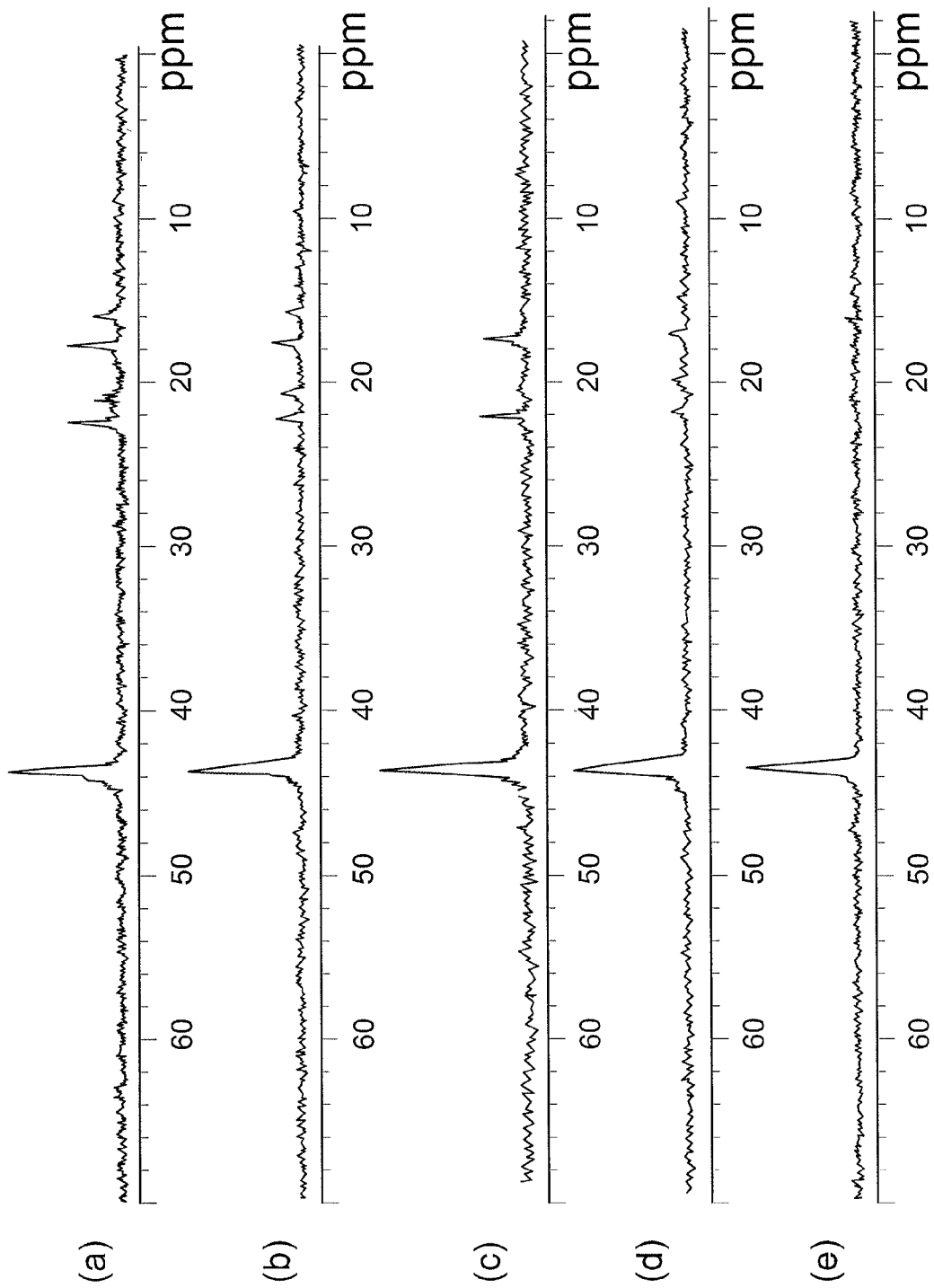
FIG. 3 is a $^{31}$P NMR reaction tracing spectrum of compound P-BNP-2a, where the time is respectively (a) 5 min, (b) 10 min, (c) 15 min, (d) 20 min, and (e) 25 min.

FIG. 3 is a $^{31}$P NMR reaction tracing spectrum. It can be known from FIG. 5 that, at 5 min, the generation of the product can observed at about 43 ppm, the unreacted DOPO is at 16-23 ppm, and at 25 min, the characteristic peak of DOPO disappears completely and only a peak of the product can be observed; that is, the compound is synthesized successfully and completely. The GPC analysis results of the product are shown in Table 1.

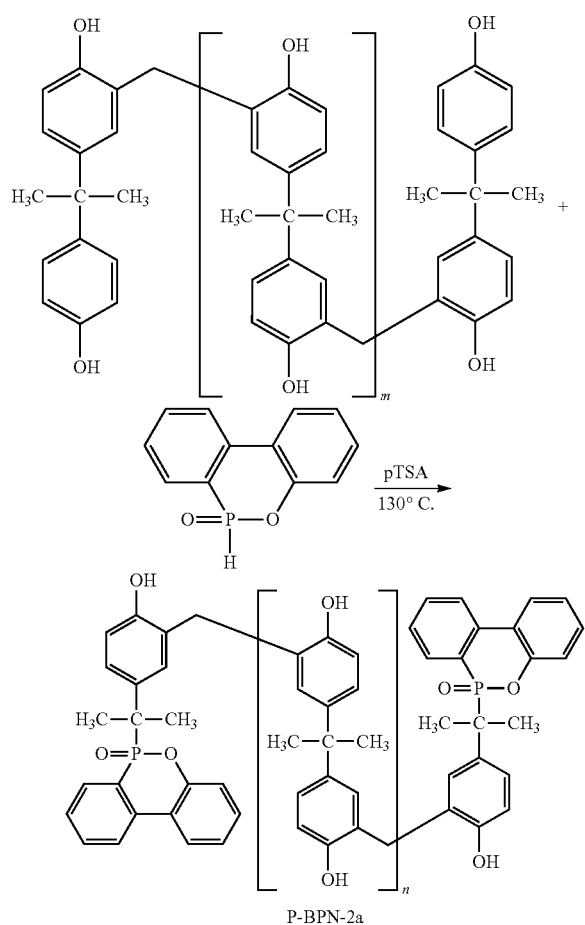

P-BPN-2a

Example 7

Synthesis of Compound P-BPN-3a

A phosphinated novolac resin (P-BPN-3a) having a phosphorus content of 3% was obtained through reaction of BPN and DOPO in the presence of an acid catalyst, and the synthesis steps were as follows. To a 0.5 L three-neck reactor equipped with a temperature indicating device, 50 g of BPN, 13.227 g of DOPO, and 2 g (BPN of 4 wt %) of toluenesulfonic acid were added. The temperature of the reaction system was maintained at 140° C. After 12 hours, the sticky reaction mixture was washed with aqueous methanol solution to remove residual toluenesulfonic acid, suction-filtered, filtered and separated, and the filter cake was dried in a vacuum oven at 100° C. to give the compound P-BPN-3a. The GPC analysis results of the compound P-BPN-3a are shown in Table 1.

Example 8

Synthesis of Compound P-BPN-5a

A phosphinated novolac resin (P-BPN-5a) having a phosphorus content of 5% was obtained through reaction of BPN and DOPO in the presence of an acid catalyst, and the synthesis steps were as follows. To a 0.5 L three-neck reactor equipped with a temperature indicating device, 50 g of BPN, 26.765 g of DOPO, and 2 g (BPN of 4 wt %) of toluenesulfonic acid were added. The temperature of the reaction system was maintained at 140° C. After 12 hours, the sticky reaction mixture was washed with aqueous methanol solution to remove residual toluenesulfonic acid, suction-filtered, filtered and separated, and the filter cake was dried in a vacuum oven at 100° C. to give the compound P-BPN-5a. The GPC analysis results of the product are shown in Table 1.

Example 9

Synthesis of Compound P-BPN-2b

A phosphinated novolac resin (P-BPN-2b) having a phosphorus content of 2% was obtained through reaction of BPN and DOPO in the presence of an acid catalyst, and the synthesis steps were as follows. To a 0.5 L three-neck reactor equipped with a temperature indicating device, 50 g of BPN, 8.102 g of DOPO, and 1 g (BPN of 2 wt %) of toluenesulfonic acid were added. The temperature of the reaction system was maintained at 130° C. After 12 hours, the sticky reaction mixture was washed with aqueous methanol solution to remove residual toluenesulfonic acid, suction-filtered, filtered and separated, and the filter cake was dried in a vacuum oven at 100° C. to give the compound P-BPN-2b. The GPC analysis results of the product are shown in Table 1.

Example 10

Synthesis of Compound P-BPN-3b

A phosphinated novolac resin (P-BPN-3b) having a phosphorus content of 3% was obtained through reaction of BPN and DOPO in the presence of an acid catalyst, and the synthesis steps were as follows. To a 0.5 L three-neck reactor equipped with a temperature indicating device, 50 g of BPN, 13.227 g of DOPO, and 1 g (BPN of 2 wt %) of toluenesulfonic acid were added. The temperature of the reaction system was maintained at 130° C. After 12 hours, the sticky reaction mixture was washed with aqueous methanol solution to remove residual toluenesulfonic acid, suction-filtered, filtered and separated, and the filter cake was dried in a vacuum oven at 100° C. to give the compound P-BPN-3b. The GPC analysis results of the product are shown in Table 1.

Example 11

Synthesis of Compound P-BPN-5b

A phosphinated novolac resin (P-BPN-5b) having a phosphorus content of 5% was obtained through reaction of BPN and DOPO in the presence of an acid catalyst, and the synthesis steps were as follows. To a 0.5 L three-neck reactor equipped with a temperature indicating device, 50 g of BPN, 26.765 g of DOPO, and 1 g (BPN of 4 wt %) of toluenesulfonic acid were added. The temperature of the reaction system was maintained at 130° C. After 12 hours, the sticky reaction mixture was washed with aqueous methanol solution to remove residual toluenesulfonic acid, suction-filtered, filtered and separated, and the filter cake was dried in a vacuum oven at 100° C. to give the compound P-BPN-5b. The GPC analysis results of the product are shown in Table 1.

Example 12

Synthesis of Compound P-BPN-2PM

A phosphinated novolac resin (P-BPN-2PM) having a phosphorus content of 2% was obtained through reaction of BPN and DOPO in the presence of an acid catalyst, and the synthesis steps were as follows. To a 0.5 L three-neck reactor equipped with a temperature indicating device, 50 g of BPN, 8.102 g of DOPO, 1 g (BPN of 2 wt %) of toluenesulfonic acid, and a solvent propylene glycol monomethyl ether were added, and the reaction temperature was raised to 100° C. After 12 hours, the mixture was added in drops into water with stirring for precipitation, and suction-filtered. The filter cake was washed with a large amount of deionized water, and then suction-filtered, and filtered and separated. The filter cake was dried in a vacuum oven at 100° C. to give the compound P-BPN-2PM. The GPC analysis results of the product are shown in Table 1.

Example 13

Synthesis of Compound P-BPN-3PM

A phosphinated novolac resin (P-BPN-3PM) having a phosphorus content of 3% was obtained through reaction of BPN and DOPO in the presence of an acid catalyst, and the synthesis steps were as follows. To a 0.5 L three-neck reactor equipped with a temperature indicating device, 50 g of BPN, 13.227 g of DOPO, 1 g (BPN of 2 wt %) of toluenesulfonic acid, and a solvent propylene glycol monomethyl ether were added, and the reaction temperature was raised to 100° C. After 12 hours, the mixture was added in drops into water with stirring for precipitation, and suction-filtered. The filter cake was washed with a large amount of deionized water, and then suction-filtered, and filtered and separated. The filter cake was dried in a vacuum oven at 100° C. to give the compound P-BPN-3PM. The GPC analysis results of the product are shown in Table 1.

Example 14

Synthesis of Compound P-BPN-5PM

A phosphinated novolac resin (P-BPN-5PM) having a phosphorus content of 5% was obtained through reaction of BPN and DOPO in the presence of an acid catalyst, and the synthesis steps were as follows. To a 0.5 L three-neck reactor equipped with a temperature indicating device, 50 g of BPN, 26.765 g of DOPO, 1 g (BPN of 2 wt %) of toluenesulfonic acid, and a solvent propylene glycol monomethyl ether were added, and the reaction temperature was raised to 100° C. After 12 hours, the mixture was added in drops into water with stirring for precipitation, and suction-filtered. The filter cake was washed with a large amount of deionized water, and then suction-filtered, and filtered and separated. The filter cake was dried in a vacuum oven at 100° C. to give the compound P-BPN-5PM. The GPC analysis results of the product are shown in Table 1.

It is indicated by the GPC results of the products of Examples 6-14 that, when the amount of the catalyst is reduced from 4% to 2%, the molecular weight of the corresponding P-BPN compound is increased significantly, that is, the reduction of the amount of the catalyst is beneficial to maintenance of high molecular weight. By adding propylene glycol monomethyl ether (DOW PM) as a solvent and reducing the reaction temperature to 100° C., a much higher molecular weight can be obtained.

Example 15

Synthesis of Compound P-BPN-EP-1

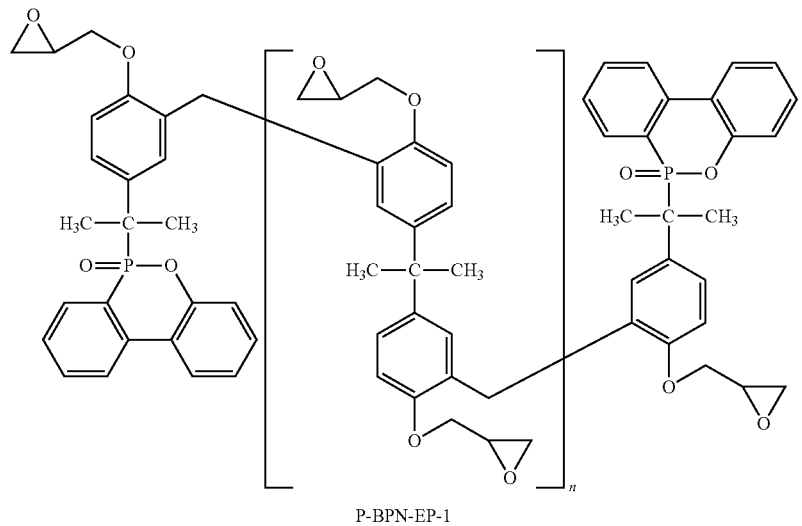

P-BPN-EP-1

21.4 g of P-BPN-5b and 92.5 g of epichlorohydrin were added into a 1 L reactor, and stirred to form a uniformly mixed solution under normal atmosphere. The reaction temperature was raised to 70° C. at an absolute pressure of 190 mmHg, and 14.6 g of 20% sodium hydroxide solution was added into the reactor in batches over 4 hours. At the same time, water in the reactor was removed by azeotropic distillation. After the reaction was completed, the epichlorohydrin and the solvent were completely distilled off under reduced pressure. The product was dissolved with methyl ethyl ketone and deionized water. Sodium chloride in the resin was washed off with water, and the solvent was completely distilled off under reduced pressure to obtain a phosphinated epoxy resin P-BPN-EP-1.

Example 16

Synthesis of Compound P-BPN-BZ-1

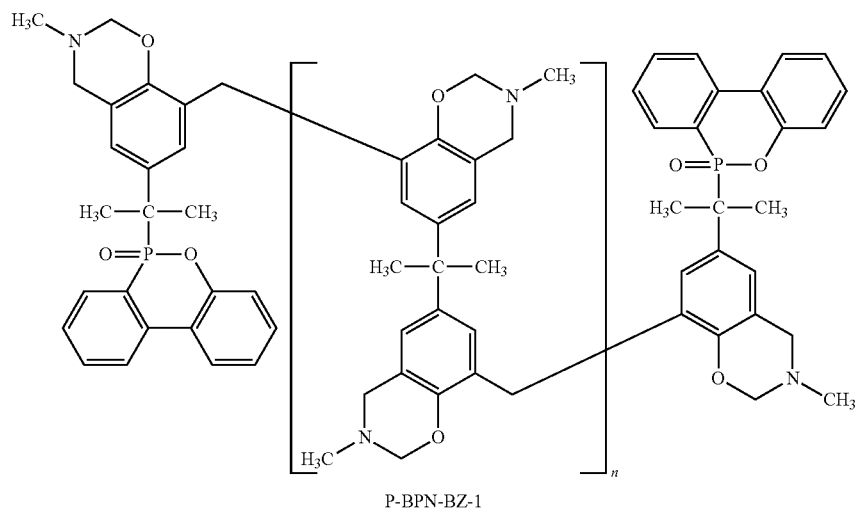

P-BPN-BZ-1

13.98 g of formaldehyde was dissolved in 12 mL of dioxane, and formulated into a solution A. 2.68 g of methylamine was dissolved in 3 mL of dioxane, and formulated into a solution B. Solution A was placed in a 100 mL reactor, which was then placed in an ice bath and fed by nitrogen gas. Solution B was added in drops into the reactor at a speed of one drop per second, the temperature was controlled at 10° C. or lower, and reaction was continued for 30 min after dropping. 11.98 g of phosphinated compound P-BPN-5b was added into the reactor, and then the temperature was raised to a reflux temperature, and reaction was continued for 10 hours. After the reaction was completed, the solvent was pumped out by a vacuum concentrator. The product was dissolved in $CH_2Cl_2$, extracted with 0.1 M sodium hydroxide and washed with deionized water three times, supplemented with anhydrous magnesium sulfate to remove water, filtered, and dried in a vacuum oven to give a solid of compound P-BPN-5-BZ-1. The yield is 85%.

Example 17

Synthesis of Compound P-BPN-OCN-1

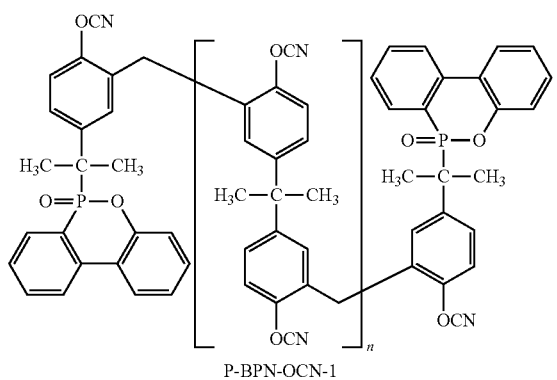

P-BPN-OCN-1

Anhydrous acetone (70 g) was added into a 1 L three-neck reactor. The reactor was cooled to −15° C., 3.102 g of BrCN was added and stirred, and at the same time, the temperature was decreased to −25° C. or lower. 2.39 g of P-BPN-5b and 2.62 g of $Et_3N$ were fully mixed and dissolved in anhydrous acetone (100 g), and then slowly added in drops into the reactor through a feed funnel. The temperature was maintained at −30° C., and the reaction was continued for 2 hours. When the reaction temperature was returned to −30° C., the reaction mixture was added in drops into deionized water to wash off ammonium bromide. After filtering, the resulting precipitate was extracted with $CH_2Cl_2/H_2O$. The organic phase was collected, and dried with anhydrous magnesium sulfate. After removal of magnesium sulfate, $CH_2Cl_2$ was removed by a rotary evaporator at room temperature, to give a solid cyanate P-BPN-OCN-1.

Application Examples 1-6

The three curing agents of Examples 6-8 were used as a curing agent for epoxy resins, and the used epoxy resins were respectively bisphenol A epoxy resin (DGEBA) and o-cresol novolac epoxy resin (CNE). The epoxy resin and the curing agent were mixed uniformly at an equivalent ratio of 1:1 in a mold, and imidazole (at an amount of 0.2 wt % of the amount of the epoxy resin) was added as curing promoter for the reaction. The glass transition temperature measured by using a DMA and results of UL-94 test are summarized in Table 2. It can be known from Table 2 that all the cured products satisfy the flame resistance level V-0 in the UL-94 flammability test.

Application Examples 7-12

The three curing agents of Embodiments 9-11 were used as a curing agent for epoxy resins, and the used epoxy resins were respectively bisphenol A epoxy resin (DGEBA) and o-cresol novolac epoxy resin (CNE). The epoxy resin and the curing agent were mixed uniformly at an equivalent ratio of 1:1 in a mold, and imidazole (at an amount of 0.2 wt % based on the epoxy resin) was added as curing promoter for the reaction. The glass transition temperature measured by a dynamic mechanical analysis (DMA) and results of UL-94 test are summarized in Table 2. It can be known from Table 2 that all the cured products satisfy the flame resistance level V-0 in the UL-94 flammability test.

Application Examples 13-18

The three curing agents of Examples 12-14 were used as a curing agent for epoxy resins, and the used epoxy resins were respectively bisphenol A epoxy resin (DGEBA) and o-cresol novolac epoxy resin (CNE). The epoxy resin and the curing agent were mixed uniformly at an equivalent ratio of 1:1 in a mold, and imidazole (at an amount of 0.2 wt % based on the epoxy resin) was added as curing promoter for the reaction. The glass transition temperature measured by DMA and results of UL-94 test are summarized in Table 2. It can be known from Table 2 that all the cured products satisfy the flame resistance level V-0 in the UL-94 flammability test.

It can be known from Table 2 that, when P-BPN is used as a flame resistant agent, all the cured products satisfy the flame resistance level V-0 in the UL-94 flammability test. When merely a phosphorus-free compound BPN is used as the curing agent, the cured product is fully combusted in the UL-94 flammability test. Additionally, when the molecular weight of the compound P-BPN is higher, the glass transition temperature of the corresponding cured product is higher.

TABLE 1

Reaction conditions and molecular weights of P-BPNs

| Curing agent | Examples | Amount of catalyst | Reaction temperature | $M_w{}^a$ | $M_n{}^a$ |
|---|---|---|---|---|---|
| BPN (commercially available) | | | | 1770 | 933 |
| P-BPN-2a | 6 | 4% | 140 | 724 | 626 |
| P-BPN-3a | 7 | 4% | 140 | 619 | 501 |
| P-BPN-5a | 8 | 4% | 140 | 513 | 405 |
| P-BPN-2b | 9 | 2% | 130 | 1398 | 899 |
| P-BPN-3b | 10 | 2% | 130 | 1186 | 765 |
| P-BPN-5b | 11 | 2% | 130 | 877 | 563 |
| P-BPN-2PM | 12 | 2% | 100 | 1509 | 1177 |
| P-BPN-3PM | 13 | 2% | 100 | 1334 | 1054 |
| P-BPN-5PM | 14 | 2% | 100 | 1099 | 897 |

[a]Number average molecular weight,
[b]Weight average molecular weight

TABLE 2

Thermal properties of cured products

| Application Example | Curing agent/epoxy resin | Tg (° C.)[a] | UL-94 level |
|---|---|---|---|
| Control 1 | BPN/DGEBA | 161 | fully combusted |
| Control 2 | BPN/CNE | 225 | fully combusted |
| 1 | P-BPN-2a/DGEBA | 135 | V-0 |
| 2 | P-BPN-3a/DGEBA | 129 | V-0 |
| 3 | P-BPN-5a/DGEBA | 120 | V-0 |
| 4 | P-BPN-2a/CNE | 160 | V-0 |
| 5 | P-BPN-3a/CNE | 150 | V-0 |
| 6 | P-BPN-5a/CNE | 148 | V-0 |
| 7 | P-BPN-2b/DGEBA | 154 | V-0 |
| 8 | P-BPN-3b/DGEBA | 146 | V-0 |
| 9 | P-BPN-5b/DGEBA | 140 | V-0 |
| 10 | P-BPN-2b/CNE | 200 | V-0 |
| 11 | P-BPN-3b/CNE | 182 | V-0 |
| 12 | P-BPN-5b/CNE | 169 | V-0 |
| 13 | P-BPN-2PM/DGEBA | 159 | V-0 |
| 14 | P-BPN-3PM/DGEBA | 153 | V-0 |
| 15 | P-BPN-5PM/DGEBA | 150 | V-0 |

TABLE 2-continued

Thermal properties of cured products

| Application Example | Curing agent/epoxy resin | Tg (° C.)[a] | UL-94 level |
|---|---|---|---|
| 16 | P-BPN-2PM/CNE | 218 | V-0 |
| 17 | P-BPN-3PM/CNE | 212 | V-0 |
| 18 | P-BPN-5PM/CNE | 205 | V-0 |

[a]Measured by a dynamic mechanical analyzer at a heating rate of 5° C./min

We claim:

1. A phosphinated compound of multifunctional phenol of formula:

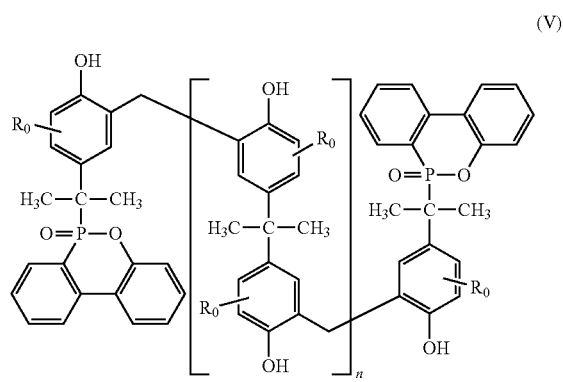

(V)

wherein $R_0$ is independently H, $C_1$-$C_6$ alkyl, $C_3$-$C_5$ cycloalkyl, F, Cl, Br or I, and n is an integer of 1 to 10.

2. The compound according to claim 1, wherein
when $R_0$ of the compound of formula (V) is H, the structural formula of the compound of formula (V) may be a phosphinated novolac resin of formula P-BPN

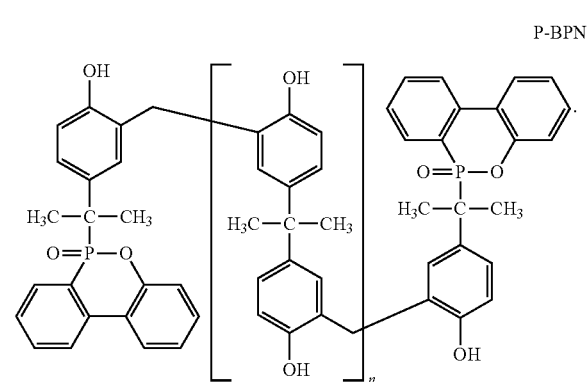

P-BPN

3. A method for preparing a multifunctional phosphinated phenol, comprising:
in the presence of an acid catalyst, reacting a DOPO compound having the following formula

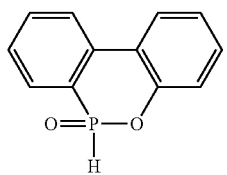
(DOPO)

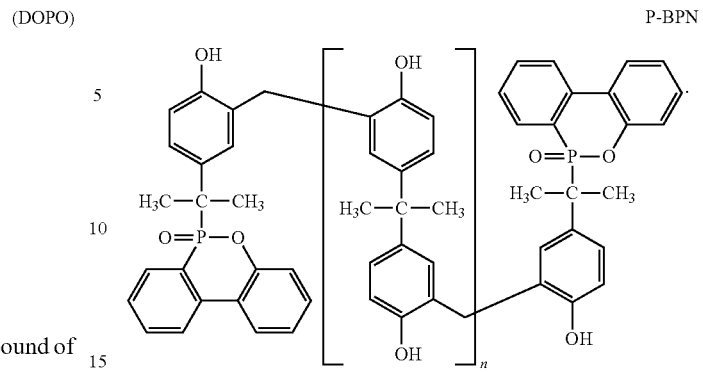
P-BPN with a compound selected from the phenolic compound of the following formula:

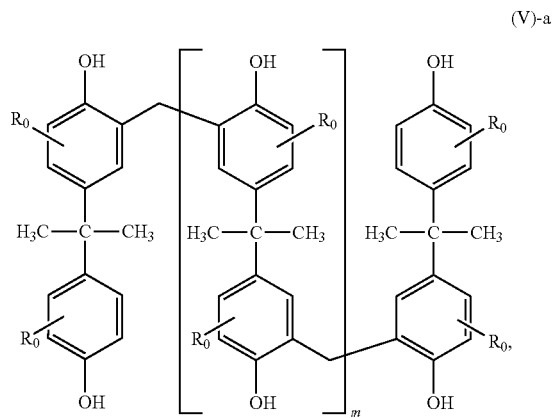
(V)-a wherein is independently H, $C_1$-$C_6$ alkyl, $C_3$-$C_6$ cycloalkyl, F, Cl, Br or I, and m is an integer of 1 to 10.

4. The method according to claim 3, wherein
when $R_0$ of the compound of formula (V)-a is H, the multifunctional phosphinated phenol product is a compound P-BPN having the following formula 5. The method according to claim 3, wherein the acid catalyst is selected from the group consisting of acetic acid, p-toluenesulfonic acid (PTSA), methanesulfonic acid, fluorosulfonic acid, trifluoromethanesulfonic acid, sulfuric acid, orthanilic acid, 3-pyridinesulfonic acid, sulfanilic acid, hydrogen chloride (HCl), hydrogen bromide (HBr), hydrogen iodide (HI), hydrogen fluoride (HF), trifluoroacetic acid ($CF_3COOH$), nitric acid ($HNO_3$), and phosphoric acid ($H_3PO_4$).

6. The method according to claim 3, wherein the amount of the acid catalyst is in the range of 0.1 wt % to 10 wt % of the amount of the phenolic compound.

7. The method according to claim 3, wherein the reaction temperature is in the range of 60° C. to 150° C.

8. The method according to claim 3, wherein the reaction solvent is selected from the group consisting of ethoxyethanol, methoxyethanol, 1-methoxy-2-propanol, propylene glycol monomethyl ether (DOW PM), dioxane, or a combination thereof.

9. A P-BPN derivative having the following formula

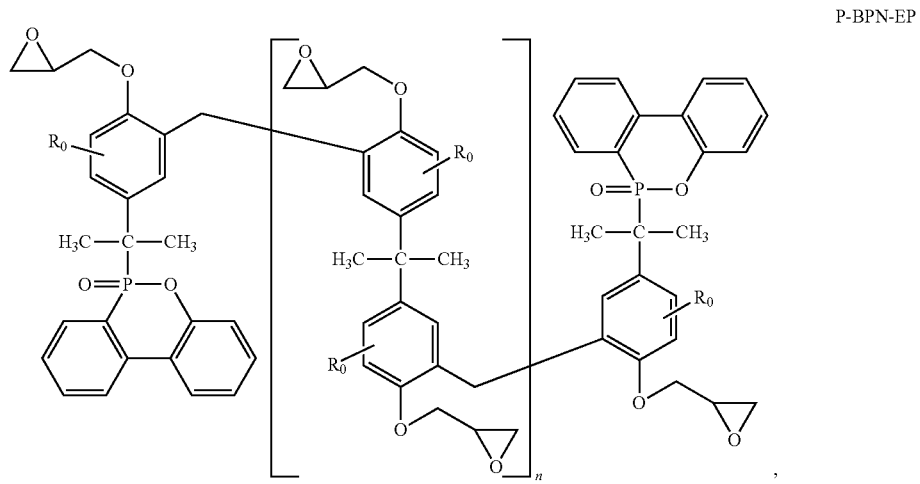
P-BPN-EP

P-BPN-BZ

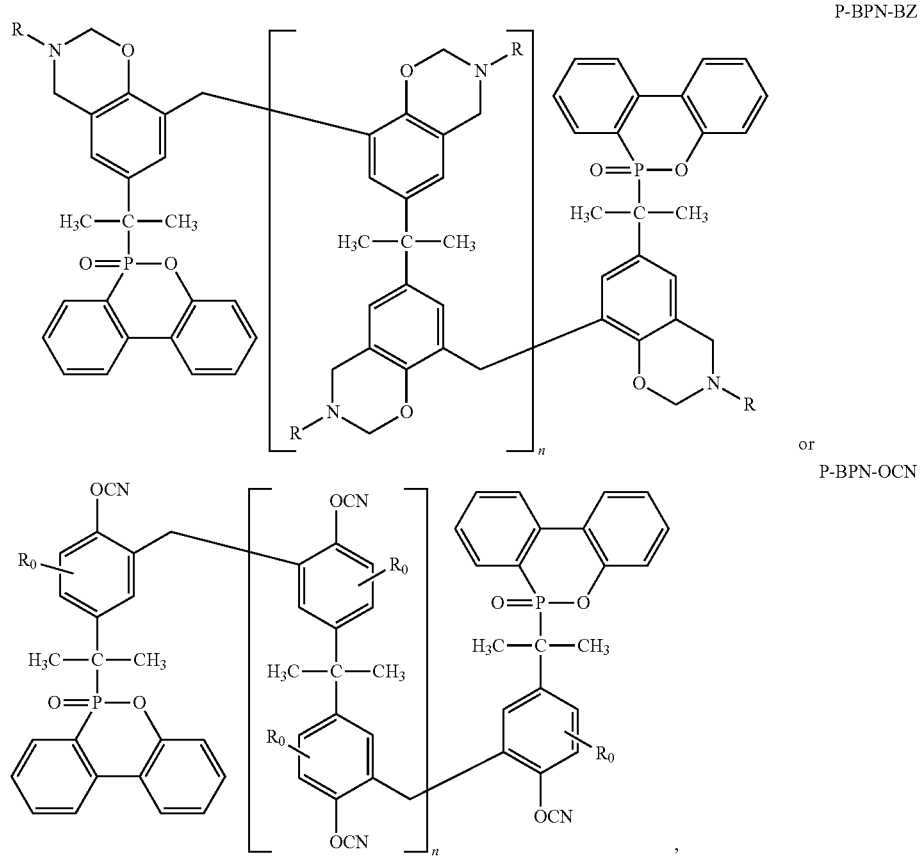

or

P-BPN-OCN wherein R₀ is $C_1$-$C_6$ alkyl, $C_3$-$C_5$ cycloalkyl, F, Cl, Br or I, and n is an integer of 1 to 10.

10. The P-BPN derivative according to claim 9, wherein when $R_0$ of the compound of formula P-BPN-EP is H, the structural formula of the compound of formula P-BPN-EP is a compound of formula P-BPN-EP-1

P-BPN-EP-1

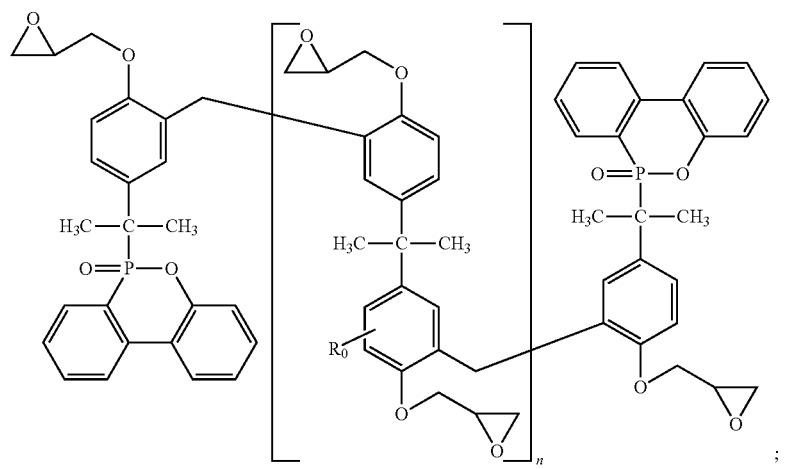

when $R_0$ of the compound of formula P-BPN-OCN is H, the structural formula of the compound of formula P-BPN-OCN is a compound of formula P-BPN-OCN-1

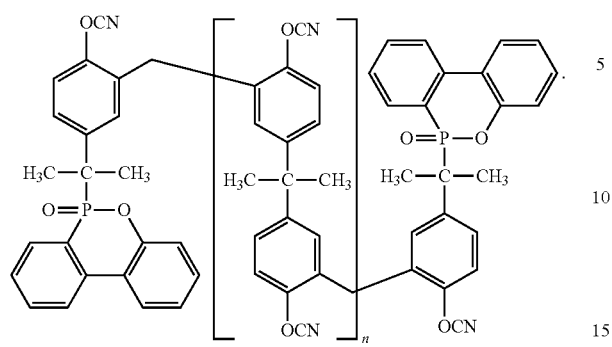
P-BPN-OCN-1
11. A preparation method of a novel P-BPN derivative, wherein the derivatives is an epoxy resin derivative (P-BPN-EP), or a cyanate derivative (P-BPN-OCN), and the chemical reactions are as shown below

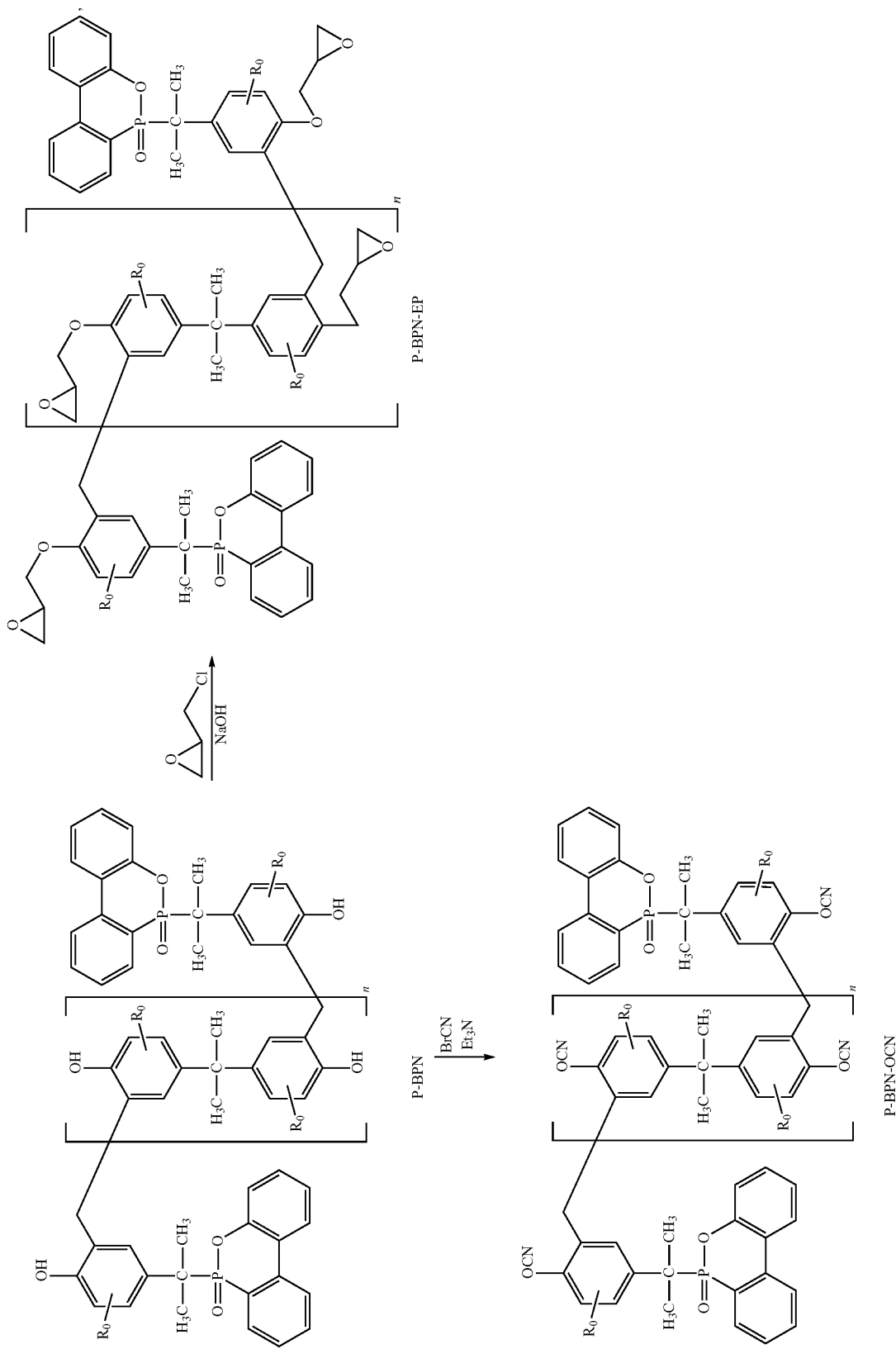

wherein $R_0$ is H, $C_1$-$C_6$ alkyl, $C_3$-$C_5$ cycloalkyl, F, Cl, Br or I, and n is an integer of 1 to 10.

12. The method according to claim 11, wherein
when $R_0$ of P-BPN is H, the resulting products are respectively epoxy resin derivative of formula P-BPN-EP 1, or a cyanate derivative of formula P-BPN-OCN-1:

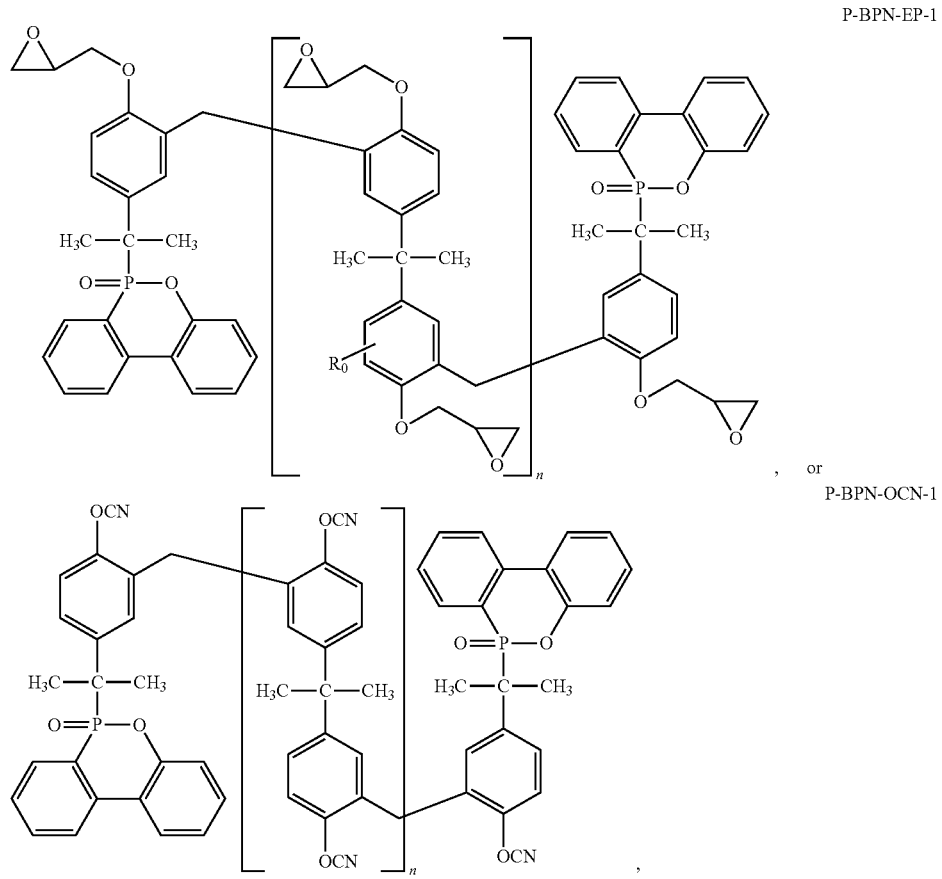

13. An epoxy resin containing a curing agent, wherein the curing agent is the compound according to claim 1.

14. An epoxy resin containing a curing agent, wherein the curing agent is the compound according to claim 2.

15. An epoxy resin containing a curing agent, wherein the curing agent is the P-BPN derivative according to claim 9.

16. An epoxy resin containing a curing agent, wherein the curing agent is the P-BPN derivative according to claim 10.

* * * * *